United States Patent
Nie et al.

(10) Patent No.: US 11,884,648 B2
(45) Date of Patent: Jan. 30, 2024

(54) HISTONE DEMETHYLASE INHIBITORS

(71) Applicant: CELGENE QUANTICEL RESEARCH, INC., San Diego, CA (US)

(72) Inventors: Zhe Nie, San Diego, CA (US); Jeffrey Alan Stafford, San Diego, CA (US); James Marvin Veal, Apex, NC (US); Michael Brennan Wallace, San Diego, CA (US)

(73) Assignee: Celgene Quanticel Research, Inc., San Diego, CA (US)

( * ) Notice: Subject to any disclaimer, the term of this patent is extended or adjusted under 35 U.S.C. 154(b) by 589 days.

(21) Appl. No.: 17/097,193

(22) Filed: Nov. 13, 2020

(65) Prior Publication Data

US 2021/0139460 A1 May 13, 2021

Related U.S. Application Data

(60) Continuation of application No. 16/819,875, filed on Mar. 16, 2020, now Pat. No. 10,870,634, which is a continuation of application No. 16/168,753, filed on Oct. 23, 2018, now Pat. No. 10,654,830, which is a division of application No. 15/487,362, filed on Apr. 13, 2017, now Pat. No. 10,150,754.

(60) Provisional application No. 62/324,813, filed on Apr. 19, 2016.

(51) Int. Cl.
*C07D 401/14* (2006.01)
*C07D 401/04* (2006.01)

(52) U.S. Cl.
CPC .......... *C07D 401/14* (2013.01); *C07D 401/04* (2013.01)

(58) Field of Classification Search
CPC .......................... C07D 401/14; C07D 401/04
See application file for complete search history.

(56) References Cited

U.S. PATENT DOCUMENTS

| | | | |
|---|---|---|---|
| 3,947,577 | A | 3/1976 | Baldwin |
| 9,676,770 | B2 | 6/2017 | Chen et al. |
| 10,150,754 | B2 | 12/2018 | Nie et al. |
| 10,654,830 | B2 | 5/2020 | Nie et al. |
| 10,870,634 | B2 | 12/2020 | Nie et al. |
| 2005/0143578 | A1 | 6/2005 | Kallender et al. |
| 2007/0287737 | A1 | 12/2007 | Goutopoulos et al. |
| 2014/0171432 | A1 | 6/2014 | Kanouni et al. |
| 2015/0164872 | A1 | 6/2015 | Nie et al. |
| 2015/0291529 | A1 | 10/2015 | Chen et al. |
| 2017/0298044 | A1 | 10/2017 | Nie et al. |
| 2019/0055221 | A1 | 2/2019 | Nie et al. |
| 2020/0216420 | A1 | 7/2020 | Nie et al. |

FOREIGN PATENT DOCUMENTS

| | | |
|---|---|---|
| CN | 101426766 A | 5/2009 |
| CN | 105026372 A | 11/2015 |
| CN | 109311822 A | 2/2019 |
| JP | 2003-530438 A | 10/2003 |
| JP | 2005-508951 A | 4/2005 |
| JP | 2009-534386 A | 9/2009 |
| JP | 2016-501882 A | 1/2016 |
| JP | 2016-503799 A | 2/2016 |
| JP | 2016-503809 A | 2/2016 |
| JP | 2019-508447 A | 3/2019 |
| JP | 2019-513803 A | 5/2019 |
| JP | 6957507 B2 | 11/2021 |
| WO | 01/78723 A1 | 10/2001 |
| WO | 03/031434 A1 | 4/2003 |
| WO | 2007/123936 A1 | 11/2007 |
| WO | 2013/143597 A1 | 10/2013 |
| WO | 2014/089364 A1 | 6/2014 |
| WO | 2014/100463 A1 | 6/2014 |
| WO | 2014/100818 A1 | 6/2014 |
| WO | 2014/151945 A1 | 9/2014 |
| WO | 2016/044342 A1 | 3/2016 |
| WO | 2017/161033 A1 | 9/2017 |
| WO | 2017/184491 A1 | 10/2017 |

OTHER PUBLICATIONS

Golub et al., Science, vol. 286, Oct. 15, 1999, pp. 531-537.*
Extended European Search Report received for European Patent Application Serial No. 17786401.4 dated Oct. 1, 2019, 8 pages.
International Preliminary Report on Patentability Chapter I received for International PCT Application Serial No. PCT/US2017/027889 dated Nov. 1, 2018, 10 pages.
International Search Report and Written Opinion dated Jul. 21, 2017, in International Application No. PCT/US2017/027889, filed Apr. 17, 2017.
Office Action received for Chinese Patent Application No. 2017800380854, dated Sep. 3, 2021, 13 pages (8 pages of English Translation and 5 pages of Official Copy).
Office Action received for Japanese Patent Application No. 2018-554567, dated Apr. 7, 2021, 5 pages (3 pages of English Translation and 2 pages of Official Copy).
Partial European Search Report received for European Patent Application No. 17786401.4, dated Aug. 14, 2019, 9 pages.

(Continued)

*Primary Examiner* — Samira J Jean-Louis
(74) *Attorney, Agent, or Firm* — Wiley Rein LLP

(57) ABSTRACT

The present embodiments provide for substituted triazolylpyridine derivative compounds, and pharmaceutical compositions comprising said compounds. The subject compounds and compositions are useful for modulating the activity of histone demethylase enzymes. Additionally, the subject compounds and compositions are useful for the treatment of cancer or other neoplastic diseases, or maladies associated with abnormal histone demethylase activity. Accordingly, the substituted triazolylpyridine derivative compounds described herein are useful in methods and medicaments for treating cancer.

4 Claims, No Drawings

(56) References Cited

OTHER PUBLICATIONS

Search Report received for Chinese Patent Application No. 2017800380854, dated Aug. 27, 2021, 2 pages (English Translation only).

Search Report received for Japanese Patent Application No. 2018-554567, dated Mar. 18, 2021, 25 pages (2 pages of English Translation & 23 pages of Official Copy).

Glaser, Keith B. "HDAC Inhibitors: Clinical Update and Mechanism-Based Potential", Biochemical Pharmacology, vol. 74, 2007, pp. 659-671.

Golub, et al. "Molecular Classification of Cancer: Class Discovery and Class Prediction by Gene Expression Monitoring", Science, vol. 286, Oct. 15, 1999, pp. 531-537.

Gura, Trisha "Cancer Models: Systems for Identifying New Drugs Are Often Faulty", Science, vol. 278, Nov. 7, 1997, pp. 1041-1042.

Johnson, J., et al. "Relationships Between Drug Activity in NCI Preclinical in Vitro and in Vivo Models and Early Clinical Trials", British Journal of Cancer, vol. 84, No. 10, 2001, pp. 1424-1431.

Ouaissi, et al. "Rationale for Possible Targeting of Histone Deacetylase Signaling in Cancer Diseases with a Special Reference to Pancreatic Cancer", Journal of Biomedicine and Biotechnology, vol. 2011, No. 315939, 2011, 8 pages.

Pearce, et al. "Failure Modes in Anticancer Drug Discovery and Development", Cancer Drug Design and Discovery, Edited by Stephen Neidle, Chapter 18, 2008, pp. 424-435.

Simone, Joseph V. "Part XIV—Oncology", Cecil Textbook of Medicine, 20th Edition, vol. 1, 1996, pp. 1004-1010.

Takai, et al. "Human Ovarian Carcinoma Cells: Histone Deacetylase Inhibitors Exhibit Antiproliferative Activity and Potently Induce Apoptosis", Cancer, vol. 101, No. 12, Dec. 15, 2004, pp. 2760-2770.

\* cited by examiner

HISTONE DEMETHYLASE INHIBITORS

RELATED APPLICATIONS

This application is a continuation of U.S. patent application Ser. No. 16/819,875, filed Mar. 16, 2020, which is a continuation of U.S. patent application Ser. No. 16/168,753, filed Oct. 23, 2018, which is a divisional of U.S. patent application Ser. No. 15/487,362, filed Apr. 13, 2017, which claims priority benefit of U.S. Provisional Application No. 62/324,813, filed Apr. 19, 2016, the contents of which are hereby incorporated by reference in their entireties for all purposes.

FIELD

The present embodiments relate generally to compounds, pharmaceutical compositions, and methods for modulating the activity of histone demethylases.

BACKGROUND

A need exists in the art for an effective treatment of cancer, neoplastic diseases, or other maladies associated with histone demethylase activity.

SUMMARY

The present embodiments provide substituted triazolylpyridine derivative compounds and pharmaceutical compositions comprising said compounds. The subject compounds and compositions are useful for the inhibition of histone demethylases. Furthermore, the subject compounds and compositions are useful for the treatment of cancer, such as pancreatic cancer, prostate cancer, breast cancer, bladder cancer, lung cancer, gastric cancer, leukemia and/or melanoma and the like. The substituted triazolylpyridine derivatives are based upon a di-substituted pyridine ring bearing at the 4-position a substituted triazolyl group which is the acid bioisostere and at the 3-position a substituted amine group or at the 2-position a substituted 1-pyrazolyl group.

At least one embodiment provides a compound having the structure of Formula I

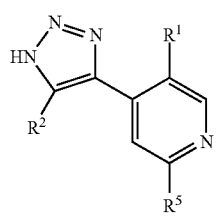

Formula I wherein the compound of Formula I includes a pharmaceutically acceptable salt thereof, and wherein
$R^1$ is halogen, —$CH_2G$, —NHG, or —OG, in which G is —X—Y, wherein X is hydrogen or $C_1$ alkyl, and Y is optionally substituted aralkyl, aralkenyl, aralkynyl, carbocyclyl, carbocyclylalkyl, heterocyclyl, heterocyclylalkyl, heteroaryl, heteroarylalkyl;
$R^2$ is halogen or —$CF_3$; and
$R^5$ is hydrogen, methyl, ethyl, isoproplyl, t-butyl, —$CHF_2$, —$CH_2F$, —$CF_3$, —$CH_2OH$, —$CHCH_3OH$, or —$C(CH_3)_2OH$.

In some embodiments of the compound of Formula I, $R^1$ is fluorine.
In some embodiments of the compound of Formula I, $R^2$ is —$CF_3$.
In some embodiments of the compound of Formula I, $R^5$ is hydrogen.
In some embodiments of Formula I, Y is optionally substituted adamantyl, benzofuranyl, 2,3-dihydrobenzofuranyl, chromanyl, indanyl, indolyl, naphthyl, 1,2-dihydronaphthyl, phenyl, pyridyl, tetrahydroquinolinyl, tetralinyl, 2,3-dihydrobenzo[b]-[1,4]dioxinyl, or thiochromanyl.
In some embodiments of the compound of Formula I, Y is phenyl substituted with alkyl, alkynyl, chloro, fluoro, fluoroalkyl, nitro; or optionally substituted aralkyl, aralkenyl, aralkynyl, carbocyclyl, carbocyclylalkyl, heterocyclyl, heterocyclylalkyl, heteroaryl or heteroarylalkyl; or —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—Ov$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$, —$R^b$—S(O)$_t OR^a$, —$R^b$—S(O)$_t R^a$, or —$R^b$—S(O)$_t N(R^a)_2$, in which each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl; each $R^b$ is independently a direct bond or a straight or branched alkyl chain; each $R^c$ is a straight or branched alkyl chain; and t is 1 or 2.

In at least one embodiment, the compound of Formula I has the structure:

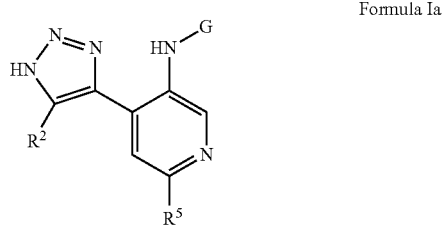

Formula Ia wherein G, $R^2$, and $R^5$ are as described above.
In some embodiments of a compound of Formula Ia, $R^2$ is —$CF_3$.
In some embodiments of a compound of Formula Ia, $R^5$ is hydrogen.
In some embodiments of a compound of Formula Ia, G is —X—Y, wherein X is hydrogen and Y is disubstituted phenyl, wherein the substituents are halogens.
In some embodiments, the compound of Formula I has the structure:

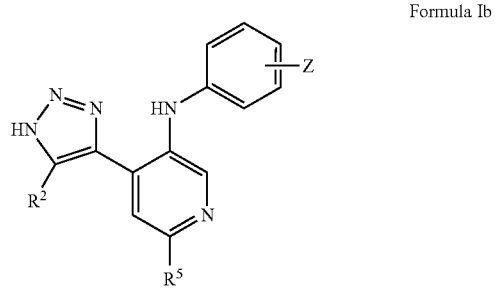

Formula Ib wherein R² and R⁵ are as described above; and

Z is independently at least one hydrogen, halogen, —OH, —CN, or optionally substituted $C_1$-$C_6$ alkyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_1$-$C_6$ alkynyl, $C_1$-$C_6$ alkenyl, $C_6$-$C_{10}$ aryl, $C_6$-$C_{10}$ aryloxy, $C_6$-$C_{10}$ aryl-S—, $C_7$-$C_{14}$ aralkoxy, heteroaryl, or hetero aryloxy.

In some embodiments of the compound of Formula Ib, Z is at least one halogen.

In some embodiments of the compound of Formula Ib, Z is at least one fluoro.

In other embodiments of the compound of Formula Ib, Z is independently at least one hydrogen, halogen, cyano, $NH_2$, $NHR^d$, $N(R^d)_2$, $NHC(O)R^d$, $NHC(O)OR^d$, $NHC(O)NHR^d$, $NHC(O)N(R^d)_2$, $NHS(O)_2R^d$, $NR^dC(O)R^d$, $NR^dC(O)OR^d$, $NR^dC(O)NHR^d$, $NR^dC(O)N(R^d)_2$, $NR^dS(O)_2R^d$, in which each $R^d$ is independently alkyl, aryl, aralkyl, carbocyclyl, heterocyclyl, heteroaryl, carbocyclylalkyl, heterocyclylalkyl, or heteroarylalkyl; or Z is independently at least one optionally substituted alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl.

In some embodiments, $R^2$ is $CF_3$.

In some embodiments, $R^5$ is hydrogen.

In some embodiments, Z is two halogens, which may be at least one F or Cl.

In some embodiments, Z is optionally substituted $C_4$-$C_{12}$ carbocyclylalkyl.

At least one embodiment provides a compound having the structure of Formula II

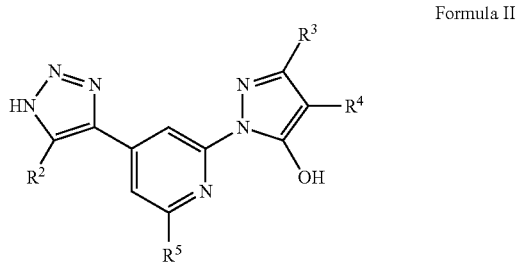

Formula II wherein a compound of Formula II includes a pharmaceutical salt thereof, and wherein $R^2$ is halogen or $CF_3$;

$R^3$ is hydrogen, halogen, —OH, —OR⁶, —N(R⁶)₂, or optionally substituted alkyl, carbocyclyl, heterocyclyl, aryl, heteroaryl, carbocyclylalkyl, heterocyclylalkyl, aralkyl, or heteroarylalkyl, in which each $R^6$ is independently hydrogen, alkyl, carbocyclyl, heterocyclyl, aryl, heteroaryl, carbocyclylalkyl, heterocyclylalkyl, aralkyl, or heteroarylalkyl;

$R^4$ is hydrogen, halogen, —OH, —OR⁶, —N(R⁶)₂, alkyl, carbocyclyl, heterocyclyl, aryl, heteroaryl, carbocyclylalkyl, heterocyclylalkyl, aralkyl, or heteroarylalkyl; and $R^5$ is hydrogen, methyl, ethyl, isoproplyl, t-butyl, —CHF₂, —CH₂F, —CF₃, —CH₂OH, —CHCH₃OH, or —C(CH₃)₂OH.

In some embodiments, $R^2$ is —CF₃.

At least one embodiment provides a pharmaceutical composition comprising a compound of Formula I (wherein reference to Formula I includes Formula Ia and Ib and pharmaceutical salts thereof) or Formula II as described herein. A pharmaceutical composition comprising a compound of Formula I or Formula II may be used to treat cancer or other disease associated with abnormal histone demethylase activity. A pharmaceutical composition comprising a compound of Formula I or Formula II may be used in the preparation of a medicament useful in treating or other disease associated with abnormal histone demethylase activity.

One embodiment provides a method for inhibiting a histone demethylase enzyme comprising contacting the histone demethylase enzyme with a compound of Formula I or Formula II. The contacting may be in vitro.

One embodiment provides a method of treating cancer or other disease associated with abnormal histone demethylase activity in a subject in need of such treatment, comprising administering to the subject a pharmaceutical composition comprising a compound of Formula I or Formula II as described herein, or a pharmaceutically acceptable salt thereof.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. Unless otherwise specified, reference to a compound includes a pharmaceutically acceptable salt thereof. In other words, the term "compound" encompasses pharmaceutically acceptable salts of that compound unless otherwise specified by context. In order that the present disclosure can be more readily understood, certain terms are defined. Additional definitions are set forth throughout the detailed description.

Definitions

"Optional" or "optionally" means that a subsequently described event or circumstance may or may not occur and that the description includes instances when the event or circumstance occurs and instances in which it does not. For example, "optionally substituted aryl" means that the aryl group may or may not be substituted and that the description includes both substituted aryl radicals and aryl radicals having no substitution. In a list of moieties, radical, or substituents, the use of "optionally substituted" at the beginning of the list indicates and all member of the list are optionally substituted. In general, unless context or language indicates otherwise, chemical groups or radicals described herein are optionally substituted.

"Alkyl" generally refers to a straight or branched hydrocarbon chain consisting solely of carbon and hydrogen atoms, containing no unsaturation, having generally from one to fifteen carbon atoms (e.g., $C_1$-$C_{15}$ alkyl). In certain embodiments, an alkyl comprises one to eight carbons (e.g., $C_1$-$C_8$ alkyl). In other embodiments, an alkyl comprises one to five carbons (e.g., $C_1$-$C_5$ alkyl). In other embodiments, an alkyl comprises one carbon atom (e.g., —$C_1$ alkyl) (e.g., methyl) or two carbons (e.g., —$C_2$ alkyl) (e.g., ethyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is typically attached to the rest of the molecule by a single bond. Unless stated otherwise, an alkyl group is optionally substituted by at least one substituent, such as halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$, —S(O)$_t$O$R^a$, —S(O)$_t$$R^a$ or —S(O)$_t$N($R^a$)$_2$, where t is 1 or 2, where each $R^a$ is independently hydrogen or optionally substituted alkyl, fluoroalkyl, carbocyclyl, carbocyclylalkyl, aryl, aralkyl, heterocyclyl, heterocyclylalkyl, heteroaryl, or heteroarylalkyl, and wherein $R^a$ is itself optionally substituted as described above. For example, in some embodiments, $R^a$ is substituted with halogen, hydroxy, methoxy, or trifluoromethyl. These and other substituents are known in the art. See, e.g., WO 2014089364, WO 2014100463, WO 2014100818, WO 2014164708, WO 2014151945, WO 2014151106, WO 2015058160, WO 2015089192, WO 2015168466, WO 2015200709, WO 2015200843, WO 2016004105, WO 2016003917, WO 2016037005, WO 2016044342, WO 2016044138, WO 2016044429, WO 2016168682, WO 2016172618.

"Alkoxy" refers to a radical bonded through an oxygen atom of the formula —O-alkyl, where alkyl is an alkyl chain as defined above; and unless stated otherwise, a moiety comprising an alkoxy group is optionally substituted as described for alkyl.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted as described for alkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise, an alkynyl group is optionally substituted as described for alkyl.

"Alkylene" "alkylene chain" "alkyl chain" or "alkyl linker" refers to a straight or branched divalent hydrocarbon chain linking the rest of the molecule to a radical group, and consisting solely of carbon and hydrogen, containing no unsaturation and having from one to twelve carbon atoms, for example, methylene, ethylene, propylene, n-butylene, and the like. Reference to alkyl may refer to such chains or linkers, as indicated by context. Similarly, "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms. These hydrocarbon chains are optionally substituted as described for alkyl.

"Aryl" refers to an aromatic monocyclic or multicyclic hydrocarbon ring system containing a delocalized (4n+2) π-electron system in accordance with the Hückel theory. The aryl contains only hydrogen and carbon, generally from five to eighteen carbon atoms, where at least one of the rings in the ring system is fully unsaturated. Aryls include benzene, fluorene, indane, indene, tetralin, and naphthalene. Unless stated otherwise, the term "aryl" or the prefix "ar-" (such as in "aralkyl") includes aryls optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$, —$R^b$—S(O)$_t$O$R^a$, —$R^b$—S(O)$_t$$R^a$, or —$R^b$—S(O)$_t$N($R^a$)$_2$, where t is 1 or 2, where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkyl or alkenylene chain, and where each of the above substituents is optionally substituted unless otherwise indicated. Additional substituents are as described for alkly.

"Aralkyl" refers to the formula —R$^c$-aryl where R$^c$ is an alkyl or alkyl chain (e.g., alkyl linker) as defined above, for example, methylene, ethylene, and the like. The alkyl chain part of the aralkyl is optionally substituted as described above for alkyl. The aryl part of the aralkyl radical is optionally substituted as described for an aryl group.

"Aralkenyl" refers to a group with the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a group bonded through an oxygen atom of the formula —O—R$^c$-aryl where R$^c$ is an alkyl chain as defined above, for example, methylene, ethylene, and the like. The alkyl chain part of the aralkyl is optionally substituted as described above for an alkyl chain. The aryl part of the aralkyloxy is optionally substituted as described above for an aryl group.

"Carbocyclyl" refers to a stable non-aromatic (saturated) monocyclic, bicyclic, or polycyclic hydrocarbon group consisting solely of carbon and hydrogen atoms, which generally includes fused or bridged ring systems, having from three to fifteen carbon atoms. In certain embodiments, a carbocyclyl comprises three to ten carbon atoms. In other embodiments, a carbocyclyl comprises three to seven carbon atoms. The carbocyclyl is attached to the rest of the molecule by single bond(s). A carbocyclyl group may be fully saturated or partially saturated. A fully saturated carbocyclyl group may also refer to a "cycloalkyl." Example monocyclic cycloalkyls include cyclopropyl, cyclobutyl, cyclopentyl, cyclohexyl, cycloheptyl, and cyclooctyl. An unsaturated carbocyclyl may also refer to a "cycloalkenyl." Example monocyclic cycloalkenyls include cyclopentenyl, cyclohexenyl, cycloheptenyl, and cyclooctenyl. Polycyclic carbocyclyls include, for example, adamantyl, norbornyl (i.e., bicyclo[2.2.1]heptanyl), norbornenyl, decalinyl, 7,7-dimethyl-bicyclo[2.2.1]-heptanyl, and the like. Unless otherwise stated, the term "carbocyclyl" includes carbocyclyls that are optionally substituted by one or more substituents independently selected and as described above.

"Carbocyclylalkyl" refers to a group of the formula —R$^c$-carbocyclyl, wherein R$^c$ is an alkyl chain, optionally substituted, as described above. Similarly, Ccrbocyclylalkynyl" refers to a group of the formula —R$^c$-carbocyclyl, where R$^c$ is an alkynylene chain, optionally substituted, as defined above. In some embodiments the carbocyclyl group is a cycloalkyl group, in which the alkynylene chain part of the carbocyclylalkynyl is optionally substituted as defined above for an alkyl chain.

"Carbocyclylalkoxy" refers to a radical bonded through an oxygen atom of the formula —O—R$^c$-carbocyclyl where R$^c$ is an alkyl chain, optionally substituted, as defined above for alkyl.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

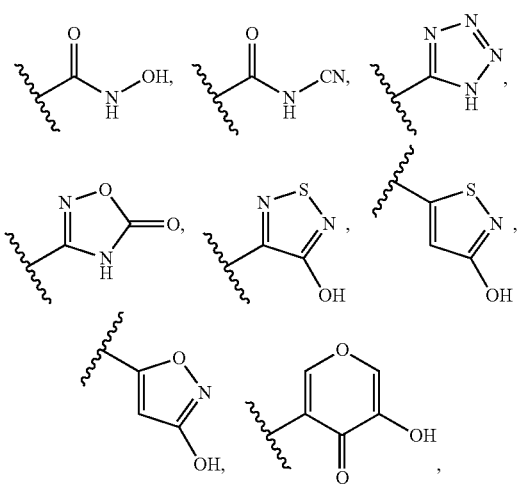

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for alkyl.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, azocanyl, chromenyl, cinnolinyl, dioxolanyl, thienyl[1,3]dithianyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxo-piperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuranyl, trithianyl, tetrahydropyranyl, thiocanyl, thiomorpholinyl, thiamorpholinyl, 1-oxo-thiomorpholinyl, and 1,1-dioxo-thio-morpholinyl. Unless stated otherwise, the term "heterocyclyl" includes heterocyclyl group as defined above that are optionally substituted by one or more substituents as described herein.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkyl chain of the heterocyclylalkyl and the heterocyclyl part of the heterocyclylalkyl group may each be optionally substituted as defined above.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkyl chain of the heterocyclylalkoxy is optionally substituted as defined above for alkyl. The heterocyclyl part of the heterocyclylalkoxy is optionally substituted as defined above for a heterocyclyl group.

Heteroaryl" refers to a moiety derived from a three- to eighteen-membered aromatic ring that generally comprises two to seventeen carbon atoms and from one to six heteroatoms selected from nitrogen, oxygen and sulfur, wherein at least one of the rings in the ring system is fully unsaturated, i.e., it contains a cyclic, delocalized (4n+2) π-electron system in accordance with the Hückel theory. The heteroaryl may be a monocyclic, bicyclic, tricyclic or tetracyclic ring system, and includes fused or bridged ring systems. The heteroatom(s) in the heteroaryl group is optionally oxidized. One or more nitrogen atoms, if present, are optionally quaternized. The heteroaryl can be attached to the rest of the molecule through any atom of the ring(s). Unless stated otherwise, heteroaryls are optionally substituted with one or more substituents as described herein.

Examples of heteroaryls include, but are not limited to, azepinyl, acridinyl, benzimidazolyl, benzin-dolyl, 1,3-benzodioxolyl, benzofuranyl, benzooxazolyl, benzo[d]-thiazolyl, benzothiadiazolyl, benzo[b][1,4]dioxepinyl, benzo[b][1,4]oxazinyl, 1,4-benzo-dioxanyl, benzonaphthofuranyl, benzo-xazolyl, benzodioxolyl, benzodioxinyl, benzopyranyl, benzopyranonyl, benzofuranyl, benzo-furanonyl, benzothienyl (benzothiophenyl), benzo-thieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[b]quinazolinyl, 5,6-dihydrobenzo[b]cinnolinyl, 6,7-dihydro-5H-benzo[6,7]-cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydro-cycloocta[d]pyridazinyl, 5,6,7,8,9,10-hexahydrocycloocta[d] pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octa-hydrobenzo[b]quin-azolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d] pyrimidinyl, pyridinyl, pyrido[3,2-d]-pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydro-quinazolinyl, 5,6,7,8-tetrahydrobenzo[4,5]thieno[2,3-d]pyrimidinyl, 6,7,8,9-tetrahydro-5H-cyclo-hepta[4,5]thieno[2,3-d]pyrimidinyl, 5,6,7,8-tetrahydropyrido[4,5-c] pyridazinyl, thiazolyl, thiadiazolyl, triazolyl, tetrazolyl, triazinyl, thieno[2,3-d]pyrimidinyl, thieno[3,2-d]pyrimi-dinyl, thieno[2,3-c]pridinyl, and thiophenyl (i.e. thienyl).

"N-heteroaryl" refers to a heteroaryl containing at least one nitrogen and where the point of attachment of the heteroaryl to the rest of the molecule is through a nitrogen atom in the heteroaryl radical. A N-heteroaryl is optionally substituted as described above.

"C-heteroaryl" refers to a heteroaryl where the point of attachment of the heteroaryl to the rest of the molecule is through a carbon atom in the heteroaryl. A C-heteroaryl is optionally substituted as described above for heteroaryl.

"Heteroarylalkyl" refers to a group of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkyl chain. If the heteroaryl is a nitrogen-containing heteroaryl, the heteroaryl is optionally attached to the alkyl radical at the nitrogen atom. The alkyl chain of the heteroarylalkoxy is optionally substituted as defined above for alkyl. The heteroaryl part of the heteroarylalkoxy is optionally substituted as defined above for heteroaryl.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

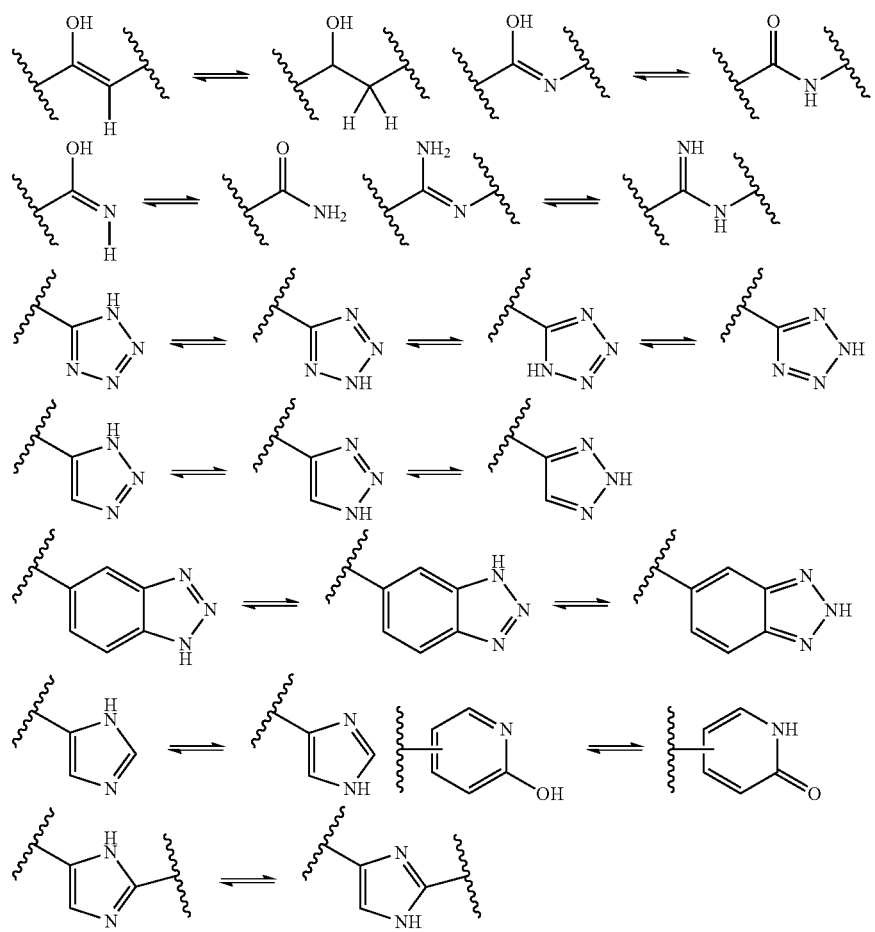

"Pharmaceutically acceptable salt" includes both acid and base addition salts. A pharmaceutically acceptable salt of any one of the compounds described herein is intended to encompass any and all pharmaceutically suitable salt forms. A pharmaceutically acceptable salt of any one of these compounds is intended to encompass any and all pharmaceutically suitable salt forms, including pharmaceutically acceptable salts such as acid and base addition salts, as are well-known in the art. See, e.g., WO 2014089364, WO 2014100463, WO 2014100818, WO 2014164708, WO 2014151945, WO 2014151106, WO 2015058160, WO 2015089192, WO 2015168466, WO 2015200709, WO 2015200843, WO 2016004105, WO 2016003917, WO 2016037005, WO 2016044342, WO 2016044138, WO 2016044429, WO 2016168682, WO 2016172618.

Further, a compound described herein may be produced or formulated as a "prodrug." Prodrugs are compounds that may be inactive when administered, but are converted under physiological conditions or by hydrolysis (i.e., in vivo) to a biologically active compound; thus prodrugs are pharmaceutically acceptable precursors of a biologically active compound. Prodrug compounds may offer advantages of solubility, tissue compatibility, or delayed release in a subject. Prodrugs also refer to use of covalently bonded carriers that release the active compound in vivo when such prodrug is administered to the subject. Prodrugs of an active compound may be prepared by modifying functional groups present in the active compound in such a way that the modifications are cleaved, either in routine manipulation or in vivo, to the parent active compound. For example, prodrugs include compounds in which a hydroxy, amino, or mercapto group is bonded to any group that, when the prodrug of the active compound is administered to a mammalian subject, cleaves to form a free hydroxy, free amino, or free mercapto group, respectively. Examples of prodrugs include acetate, carboxylate, formate, and benzoate derivatives of alcohol or amine functional groups in the active compounds. See, e.g., Bundgard, DESIGN OF PRODRUGS, at 7-9, 21-24 (Elsevier, Amsterdam, 1985); Higuchi et al., *Pro drugs as Novel Delivery Systems,* 14 A.C.S. Symposium Series; BIOREVERSIBLE CARRIERS IN DRUG DESIGN (Edward B. Roche (Ed.), Am. Pharm. Assoc, and Pergamon Press, 1987).

Accordingly, and as used herein, reference to "compound" or "Formula" or "compound of Formula I," and the like, includes within that reference a pharmaceutically acceptable salt, hydrate, solvate, N-oxide, stereoisomer, tautomer, radioisotopically enriched or deuterated version, or prodrug thereof.

As used herein, "treatment" or "treating," or "palliating" or "ameliorating" are used interchangeably herein. These terms refer to an approach for obtaining beneficial or desired results including but not limited to therapeutic benefit or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "modulating" means, in relation to histone demethylation, a process in which the enzymatic activity of the histone demethylase is changed by contact with a substituted triazolylpyridine derivative compound described herein in comparison with a control; the activity level may be increased or decreased (i.e., inhibited) depending on the particular cellular or molecular context of the histone demethylase. The original, unmodulated activity may be of any kind of activity, including absence of any activity. The term "modulating the activity" includes, for example, any change of histone demethylase activity that leads to increased function of a cellular pathway (e.g., a signaling pathway), including pathways that conclude with apoptosis. The enzymatic activity can increase from zero (absent or immeasurable activity) to a certain amount; or, more typically, can decrease from a certain amount to and immeasurable small amount or zero. Modulating activity can be expressed, for example, as $IC_{50}$ when a substituted triazolylpyridine derivative compound inhibits enzymatic activity of a histone demethylase (see Examples).

Substituted Triazolylpyridine Derivative Compounds

Substituted compounds are described herein that inhibit a histone demethylase enzyme. These compounds, and compositions comprising these compounds, are useful for the treatment of cancer and neoplastic diseases. The compounds described herein may, therefore, be useful for treating pancreatic cancer, prostate cancer, breast cancer, bladder cancer, lung cancer, gastric cancer, leukemia or melanoma and the like. As noted above: unless stated otherwise all references to a compound include the pharmaceutically acceptable salts thereof.

At least one embodiment provides a compound having the structure of Formula I

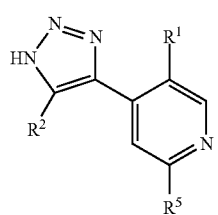

Formula I wherein the compound of Formula I includes pharmaceutical salts thereof, and wherein $R^1$ is halogen, $CH_2G$, NHG, or OG, wherein
  G is hydrogen, alkyl, or —X—Y, in which
    X is hydrogen or —$C_1$ alkylene, and
    Y is optionally substituted aralkyl, aralkenyl, aralkynyl, carbocyclyl, carbocyclylalkyl, heterocyclyl, heterocyclylalkyl, heteroaryl, heteroarylalkyl, adamantyl, benzofuranyl, 2,3-dihydrobenzofuranyl, chromanyl, indanyl, indolyl, naphthyl, optionally substituted 1,2-dihydronaphthyl, phenyl, pyridyl, tetrahydroquinolinyl, tetralinyl, 2,3-dihydrobenzo[b][1,4]dioxinyl or thiochromanyl, or —$R^b$—$OR^a$, —$R^b$—OC(O)—$R^a$, —$R^b$—OC(O)—$OR^a$, —$R^b$—OC(O)—$N(R^a)_2$, —$R^b$—N$(R^a)_2$, —$R^b$—C(O)$R^a$, —$R^b$—C(O)$OR^a$, —$R^b$-Ov$R^c$—C(O)$N(R^a)_2$, —$R^b$—N$(R^a)$C(O)$OR^a$, —$R^b$—N$(R^a)$C(O)$R^a$, —$R^b$—N$(R^a)$S(O)$_tR^a$, —$R^b$—S(O)$_tOR^a$, —$R^b$—S(O)$_tOR^a$, or —$R^b$—S(O)$_tN(R^a)_2$, wherein
  each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl,
  each $R^b$ is independently a direct bond or a straight or branched alkylene or alkenylene chain,
  each $R^c$ is a straight or branched alkylene or alkenylene chain; and
  t is 1 or 2;

$R^2$ is halogen or $CF_3$; and
$R^5$ hydrogen, methyl, ethyl, isoproplyl, t-butyl, —$CHF_2$, —$CH_2F$, —$CF_3$, —$CH_2OH$, —$CHCH_3OH$, or —$C(CH_3)_2OH$.

In some embodiments of the compound of Formula I, $R^1$ is fluoro.

In some embodiments of the compound of Formula I, $R^2$ is $CF_3$.

In some embodiments of the compound of Formula I, $R^5$ is hydrogen.

In some embodiments of the compound of Formula I, Y is phenyl optionally substituted with alkyl, alkynyl, chloro, fluoro, fluoroalkyl, nitro or optionally substituted aralkyl, aralkenyl, aralkynyl, carbocyclyl, carbocyclylalkyl, heterocyclyl, heterocyclylalkyl, heteroaryl, heteroarylalkyl, or —$R^b$—$OR^a$, —$R^b$—OC(O)—$R^a$, —$R^b$—OC(O)—$OR^a$, —$R^b$—OC(O)—$N(R^a)_2$, —$R^b$—N$(R^a)_2$, —$R^b$—C(O)$R^a$, —$R^b$—C(O)$OR^a$, —$R^b$—Ov$R^c$—C(O)$N(R^a)_2$, —$R^b$—N$(R^a)$C(O)$OR^a$, —$R^b$—N$(R^a)$C(O)$R^a$, —$R^b$—N$(R^a)$S(O)$_tR^a$, —$R^b$—S(O)$_tOR^a$, —$R^b$—S(O)$_tOR^a$, or —$R^b$—S(O)$_tN(R^a)_2$, in which each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl; each $R^b$ is independently a direct bond or a straight or branched alkyl or alkenyl chain; each $R^c$ is a straight or branched alkyl or alkenyl chain; and t is 1 or 2.

Another embodiment provides a compound of Formula I wherein $R^1$ is alkyl. Another embodiment provides a compound of Formula I, wherein $R^1$ is methyl.

Another embodiment provides a compound of Formula I, wherein $R^1$ is carbocyclyl or carbocyclylalkyl. Another embodiment provides a compound of Formula I, wherein $R^1$ is carbocyclyl($C_1$-$C_6$ alkyl). Another embodiment provides a compound of Formula I, wherein $R^1$ is carbocyclylethyl or carbocyclylmethyl.

Another embodiment provides a compound of Formula I, wherein $R^1$ is carbocyclyl($C_1$-$C_6$ alkyl) and the carbocyclyl is 1,2,3,4-tetrahydronaphthyl optionally substituted with one or more groups selected from halogen, hydroxy, —CN, alkyl, alkoxy, alkylamino, aryl, carbocyclyl, heterocyclyl, carbocyclylalkyl, or heterocyclylalkyl.

Another embodiment provides a compound of Formula I wherein $R^1$ is optionally substituted heterocyclyl or heterocyclylalkyl.

Another embodiment provides a compound of Formula I wherein $R^1$ is optionally substituted heteroaryl or heteroarylalkyl.

Another embodiment provides a compound of Formula I wherein $R^1$ is optionally substituted aryl or aralkyl.

Another embodiment provides a compound of Formula I wherein $R^1$ is optionally substituted aralkyl, and the aralkyl is aryl($C_1$-$C_6$ alkyl). Another embodiment provides a compound of Formula I wherein $R^1$ is optionally substituted aralkyl, the aralkyl is arylethyl or arylmethyl.

Another embodiment provides a compound of Formula I, wherein Y is optionally substituted aryl or aralkyl, and the aryl is phenyl optionally substituted with at least one halogen, hydroxy, —CN, alkyl, alkoxy, alkylamino, aryl, carbocyclyl, heterocyclyl, carbocyclylalkyl, or heterocyclylalkyl.

Another embodiment provides a compound of Formula I, wherein Y is optionally substituted aryl or aralkyl, and the aryl is naphthyl optionally substituted with at least one halogen, hydroxy, —CN, alkyl, alkoxy, alkylamino, aryl, carbocyclyl, heterocyclyl, carbocyclylalkyl, or heterocyclylalkyl.

Another embodiment provides a compound of Formula I wherein Y is hydrogen, halogen, —CN, or an alkyl optionally substituted with at least one fluoro. Another embodiment provides a compound of Formula I wherein X is hydrogen. Another embodiment provides a compound of Formula I wherein $R^1$ is fluoro. Another embodiment provides a compound of Formula I wherein $R^1$ is chloro. Another embodiment provides a compound of Formula I wherein $R^1$ is iodo. Another embodiment provides a compound of Formula I wherein Y is —CN. Another embodiment provides a compound of Formula I wherein $R^2$ is —$CF_3$.

Another embodiment provides a compound of Formula I wherein $R^1$ is hydrogen or aryl. Another embodiment provides a compound of Formula I wherein $R^1$ is hydrogen. Another embodiment provides a compound of Formula I wherein $R^1$ is aryl. Another embodiment provides a compound of Formula I wherein $R^1$ is aryl and the aryl is phenyl optionally substituted with at least one halogen, hydroxy, —CN, alkyl, alkoxy, —O-(cycloalkylalkyl), alkylamino, aryl, carbocyclyl, heterocyclyl, carbocyclylalkyl, or heterocyclylalkyl. Another embodiment provides a compound of Formula I wherein $R^1$ is aryl, and the aryl is a phenyl is substituted with one or more groups selected from halogen, alkoxy, or —O-(cycloalkylalkyl). Another embodiment provides a compound of Formula I wherein $R^5$ is hydrogen.

In at least one embodiment, the compound of Formula I has the structure:

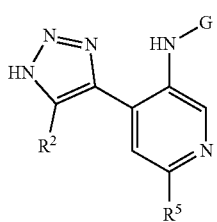

Formula Ia wherein G, $R^2$, and $R^5$ are as described above.

In at least one embodiment, the compound of Formula I has the structure:

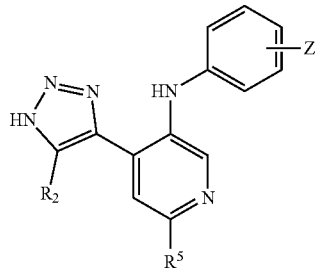

Formula Ib wherein $R^2$ and $R^5$ are as described above; and

Z is independently at least one hydrogen, halogen, —OH, —CN, or optionally substituted $C_1$-$C_6$ alkyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_1$-$C_6$ alkynyl, $C_1$-$C_6$ alkenyl, $C_6$-$C_{10}$ aryl, $C_6$-$C_{10}$ aryloxy, $C_6$-$C_{10}$ aryl-S—, $C_7$-$C_{14}$ aralkoxy, heteroaryl, or heteroaryloxy.

In some embodiments of a compound of Formula Ib, Z is at least one halogen. In some embodiments of the compound, Z is at least one fluoro. In some embodiments, $R^2$ is $CF_3$. In some embodiments, $R^5$ is hydrogen.

In another embodiment of a compound of Formula Ib, Z is independently at least one hydroxy, halogen, cyano, $NH_2$, $NHR^d$, $N(R^d)_2$, NHC(O)$R^d$, NHC(O)O$R^d$, NHC(O)NH$R^d$, NHC(O)N($R^d$)$_2$, NHS(O)$_2R^d$, $NR^dC(O)R^d$, $NR^dC(O)OR^d$, $NR^dC(O)NHR^d$, $NR^dC(O)N(R^d)_2$, $NR^dS(O)_2R^d$, or optionally substituted alkyl, alkenyl, alkynyl, alkoxy, aryl, aryloxy, aralkyl, carbocyclyl, heterocyclyl, heteroaryl, carbocyclylalkyl, heterocyclylalkyl, or heteroarylalkyl; in which each $R^d$ is independently alkyl, aryl, aralkyl, carbocyclyl, heterocyclyl, heteroaryl, carbocyclylalkyl, heterocyclylalkyl or heteroarylalkyl.

In some embodiments of a compound of Formula Ib, $R^2$ is —$CF_3$, one of Z is fluoro; one of Z is an optionally substituted straight, branched, or cyclic $C_1$-$C_6$ alkyl, and $R^5$ is hydrogen. In some embodiments of the compound, $R^2$ is —$CF_3$, one of Z is fluoro and one of Z is an optionally substituted straight, branched, or cyclic $C_1$-$C_6$ alkoxy, and $R^5$ is hydrogen. In some embodiments of the compound, $R^2$ is —$CF_3$, one of Z is fluoro, one of Z is trifluoromethyloxy, and $R^5$ is hydrogen. In some embodiments of the compound of Formula I, $R^2$ is —$CF_3$, one of Z is fluoro and one of Z is phenylmethoxy, and $R^5$ is hydrogen. In some embodiments of the compound, $R^2$ is $CF_3$, one of Z is fluoro, one of Z is —$NHR^d$ or —$N(R^d)_2$, and $R^5$ is hydrogen. In some embodiments of the compound, $R^2$ is —$CF_3$, $R^1$ is —NHG, wherein G is —X-Y and X is —$C_1$ alkylene, and $R^5$ is hydrogen.

At least one embodiment provides a compound having the structure of Formula II:

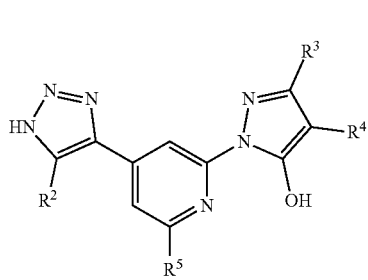

Formula II wherein a compound of Formula II includes pharmaceutically acceptable salts thereof, and wherein $R^2$ is halogen or —$CF_3$;

$R^3$ and $R^4$ are each independently hydrogen, halogen, —OH, —$OR^6$, —$N(R^6)_2$, alkyl, carbocyclyl, heterocyclyl, aryl, heteroaryl, carbocyclylalkyl, heterocyclylalkyl, aralkyl, or heteroarylalkyl, in which each $R^6$ is independently hydrogen, alkyl, carbocyclyl, heterocyclyl, aryl, heteroaryl, carbocyclylalkyl, heterocyclylalkyl, aralkyl, or heteroarylalkyl; and $R^5$ is hydrogen, methyl, ethyl, isoproplyl, t-butyl, —$CHF_2$, —$CH_2F$, —$CF_3$, —$CH_2OH$, —$CHCH_3OH$, or —$C(CH_3)_2OH$.

Some embodiments provide a compound of Formula II in which $R^2$ is —$CF_3$. Some embodiments provide a compound of Formula II wherein $R^5$ is hydrogen.

Other embodiments provide a compound of Formula II wherein $R^4$ is optionally substituted $C_1$-$C_4$ alkyl. Another embodiment provides a compound of Formula II wherein $R^4$ is $C_1$-$C_4$ alkyl, and the alkyl is substituted with at least one fluoro. Another embodiment provides a compound of Formula II wherein $R^4$ is —$CH_2F$, —$CHF_2$, or —$CF_3$. Another embodiment provides a compound of Formula II wherein $R^4$ is —$CF_3$. Another embodiment provides a compound of Formula II wherein $R^5$ is H.

Another embodiment provides the compound of Formula II wherein $R^4$ is aryl. Another embodiment provides the compound of Formula II, wherein $R^4$ is heteroaryl. Another embodiment provides the compound of Formula II wherein $R^4$ is aryl, and each aryl is independently optionally substituted with halogen, alkoxy, carbocyclyloxy, heterocyclyloxy, aryloxy, heteroaryloxy, carbocyclylalkoxy, heterocyclylalkoxy, aralkyloxy, or heteroarylalkoxy. Another embodiment provides the compound of Formula II wherein $R^4$ is aryl, and the aryl is optionally substituted with halogen, alkoxy, carbocyclyloxy heterocyclyloxy, aryloxy, heteroaryloxy, carbocyclylalkoxy, heterocyclylalkoxy, aralkoxy, or heteroarylalkoxy.

Another embodiment provides a compound of Formula II wherein $R^3$ is hydrogen. Another embodiment provides a compound of Formula II wherein $R^3$ is alkyl. Another embodiment provides a compound of Formula II wherein $R^2$ is methyl.

Another embodiment provides a compound of Formula II, wherein $R^3$ is optionally substituted carbocyclyl or carbocyclylalkyl. Another embodiment provides a compound of Formula II, or a pharmaceutically acceptable salt thereof, wherein $R^3$ is carbocyclyl($C_1$-$C_6$ alkyl). Another embodiment provides a compound of Formula II wherein $R^3$ is carbocyclyl($C_1$-$C_6$ alkyl), in which the $C_1$-$C_6$ alkyl is ethyl or methyl.

Another embodiment provides a compound of Formula II, wherein $R^3$ is optionally substituted carbocyclyl($C_1$-$C_6$ alkyl), and the carbocyclyl is 1,2,3,4-tetrahydronaphthyl optionally substituted with at least one halogen, hydroxy, —CN, alkyl, alkoxy, cycloalkylalkoxy, alkylamino, aryl, carbocyclyl, heterocyclyl, carbocyclylalkyl, or heterocyclylalkyl.

Another embodiment provides a compound of Formula II, or a pharmaceutically acceptable salt thereof, wherein $R^3$ is optionally substituted heterocyclyl or heterocyclylalkyl. Another embodiment provides a compound of Formula II, or a pharmaceutically acceptable salt thereof, wherein $R^3$ is optionally substituted heterocyclyl($C_1$-$C_6$ alkyl).

Another embodiment provides a compound of Formula II wherein $R^3$ is optionally substituted heteroaryl or heteroarylalkyl. Another embodiment provides a compound of Formula II wherein $R^3$ is optionally substituted heterocyclylalkyl, and $R^4$ and $R^5$ are hydrogen. Another embodiment provides a compound of Formula II wherein $R^3$ is optionally substituted cyclylalkyl, and $R^4$ and $R^5$ are hydrogen. Another embodiment provides a compound of Formula II wherein $R^3$ is phenyloxymethyl and $R^4$ and $R^5$ are hydrogen.

Another embodiment provides a compound of Formula II, wherein $R^3$ is optionally substituted heteroaryl or heteroarylalkyl, and the heteroaryl is pyridine or pyrimidine optionally substituted with at least one halogen, hydroxy, —CN, alkyl, alkoxy, cycloalkylalkoxy, alkamino, aryl, carbocyclyl, heterocyclyl, carbocyclylalkyl, or heterocyclylalkyl.

Another embodiment provides a compound of Formula II, wherein $R^3$ is optionally substituted heteroaryl, and the heteroaryl is a chromanyl optionally substituted with at least one halogen, hydroxy, —CN, alkyl, alkoxy, cycloalkylalkoxy, alkylamino, aryl, carbocyclyl, heterocyclyl, carbocyclylalkyl, or heterocyclylalkyl.

Another embodiment provides a compound of Formula II wherein $R^3$ is optionally substituted heteroarylalkyl, and the heteroarylalkyl comprises a chromanyl optionally substituted with at least one halogen, hydroxy, —CN, alkyl, alkoxy, cycloalkylalkoxy, alkylamino, aryl, carbocyclyl, heterocyclyl, carbocyclylalkyl, or heterocyclylalkyl. Another embodiment provides a compound of Formula II wherein $R^3$ is ethyl or methyl. Another embodiment provides a compound of Formula II wherein $R^3$ is aryl or aralkyl. Another embodiment provides the compound of Formula II wherein $R^5$ is hydrogen.

Another embodiment provides a compound of Formula II wherein $R^3$ is optionally substituted aryl or aralkyl, and the aryl is a phenyl optionally substituted with at least one halogen, hydroxy, —CN, alkyl, alkoxy, cycloalkylalkoxy, alkamino, aryl, carbocyclyl, heterocyclyl, carbocyclylalkyl, or heterocyclylalkyl. Another embodiment provides a compound of Formula II wherein $R^2$ is aryl or aralkyl, and the aryl is phenyl optionally substituted with at least one halogen, alkoxy, or alkyl.

Another embodiment provides a compound of Formula II wherein $R^3$ is optionally substituted aralkyl, and the aralkyl is aryl($C_1$-$C_6$ alkyl). Another embodiment provides a compound of Formula II wherein $R^3$ is aralkyl, the aralkyl is aryl($C_1$-$C_6$ alkyl), and the aryl is phenyl optionally substituted with one or more of halogen, hydroxy, —CN, alkyl, alkoxy, cycloalkylalkoxy, alkylamino, aryl, carbocyclyl, heterocyclyl, carbocyclylalkyl, or heterocyclylalkyl. Another embodiment provides a compound of Formula II wherein $R^3$ is aralkyl, the aralkyl is aryl($C_1$-$C_6$ alkyl), and the ($C_1$-$C_6$ alkyl) is ethyl or methyl.

Another embodiment provides a compound of Formula II wherein $R^3$ is aralkyl, and the aralkyl comprises a naphthyl optionally substituted with at least one halogen, hydroxy, —CN, alkyl, alkoxy, cycloalkylalkoxy, alkylamino, aryl, carbocyclyl, heterocyclyl, carbocyclylalkyl, or heterocyclylalkyl. Another embodiment provides a compound of Formula II wherein the aralkyl further comprises a —$C_1$ alkylene, or a —$C_2$ alkylene.

Another embodiment provides a compound of Formula II, wherein $R^1$ or $R^5$ are hydrogen. Another embodiment provides a compound of Formula II, wherein both $R^1$ and $R^5$ are hydrogen.

Another embodiment provides a compound of Formula II wherein $R^3$ is aryl. Another embodiment provides a compound of Formula II wherein $R^3$ is hydrogen or aryl.

Another embodiment provides a compound of Formula II, or a pharmaceutically acceptable salt thereof, wherein $R^3$ is aryl, and the aryl is a phenyl optionally substituted with one or more groups selected from halogen, hydroxy, —CN, alkyl, alkoxy, cycloalkylalkoxy, alkylamino, aryl, carbocyclyl, heterocyclyl, carbocyclylalkyl, or heterocyclylalkyl. Another embodiment provides a compound of Formula II, or a pharmaceutically acceptable salt thereof, wherein $R^1$ is aryl, and the aryl is a phenyl optionally substituted with one or more groups selected from halogen, alkoxy, or cycloalkylalkoxy.

In some embodiments, a compound as disclosed herein has the structure provided in Table 1:

TABLE 1

| Chemical Synthesis Example | Structure | Name |
|---|---|---|
| 1 | | 3-fluoro-4-[5-(trifluoromethyl)-1H-1,2,3-triazol-4-yl]pyridine |
| 2 | | N-(5-chloro-2-fluorophenyl)-4-[5-(trifluoromethyl)-1H-1,2,3-triazol-4-yl]pyridin-3-amine |
| 3 | | N-[(1,2,3,4-tetrahydronaphthalen-1-yl)methyl]-4-[5-(trifluoromethyl)-1H-1,2,3-triazol-4-yl]pyridin-3-amine |
| 4 | | 3-[(4-chlorophenyl)methyl]-1- {4-[5-(trifluoromethyl)-1H-1,2,3-triazol-4-yl]pyridin-2-yl}-1H-pyrazol-5-ol |

In some embodiments, the compound disclosed herein has the structure provided in Table 2, where R is Cl, F, or $CF_3$.

TABLE 2

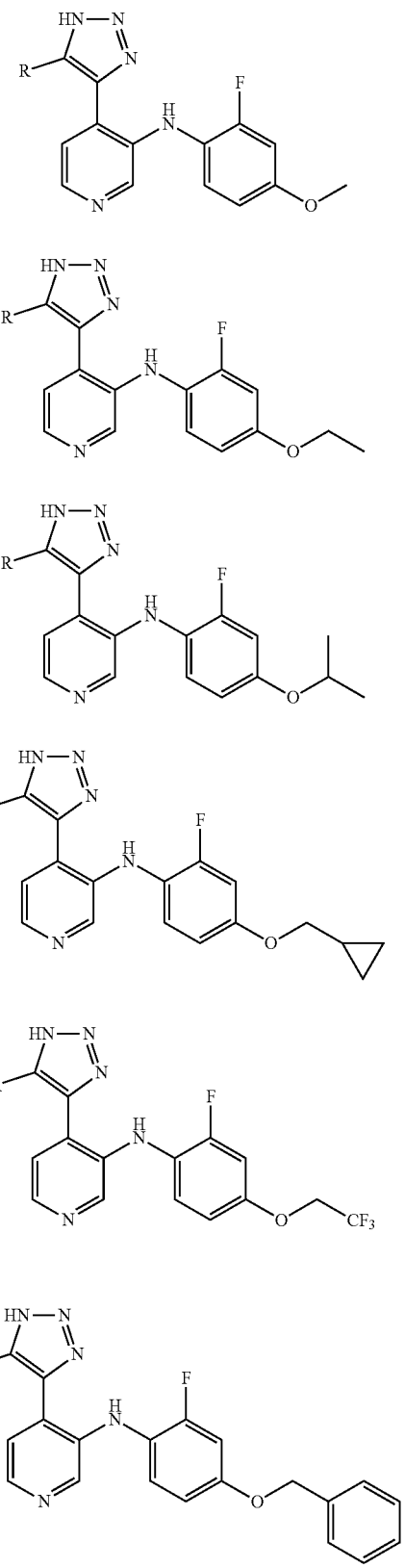

TABLE 2-continued

TABLE 2-continued
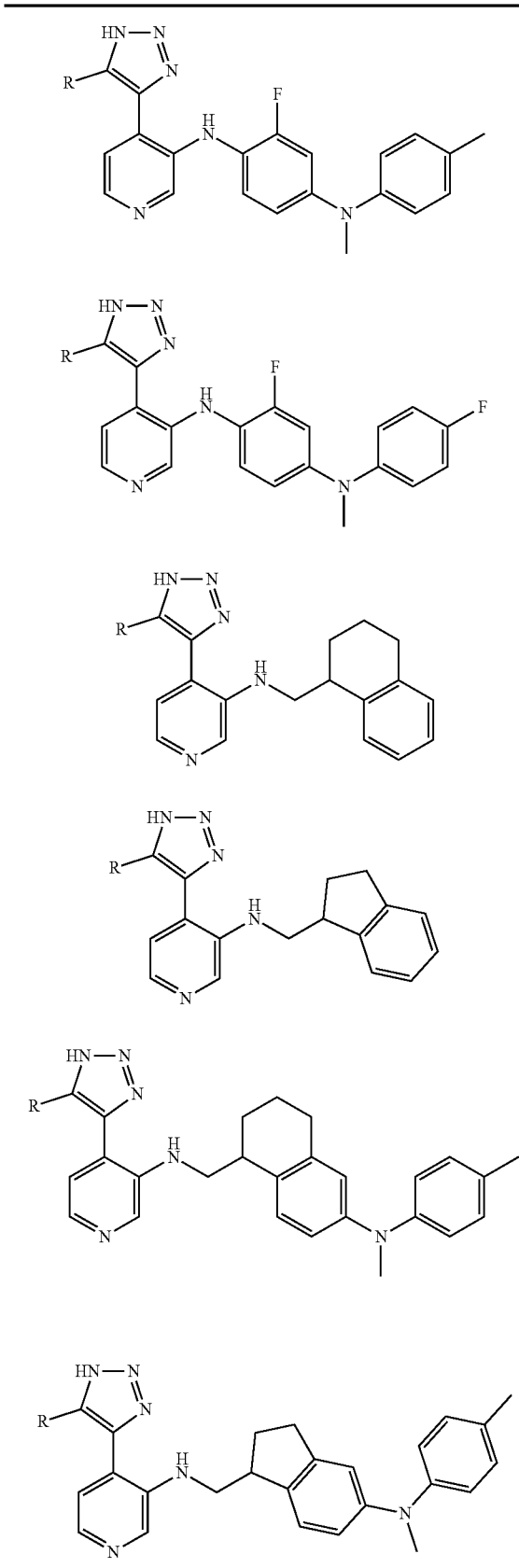
TABLE 2-continued
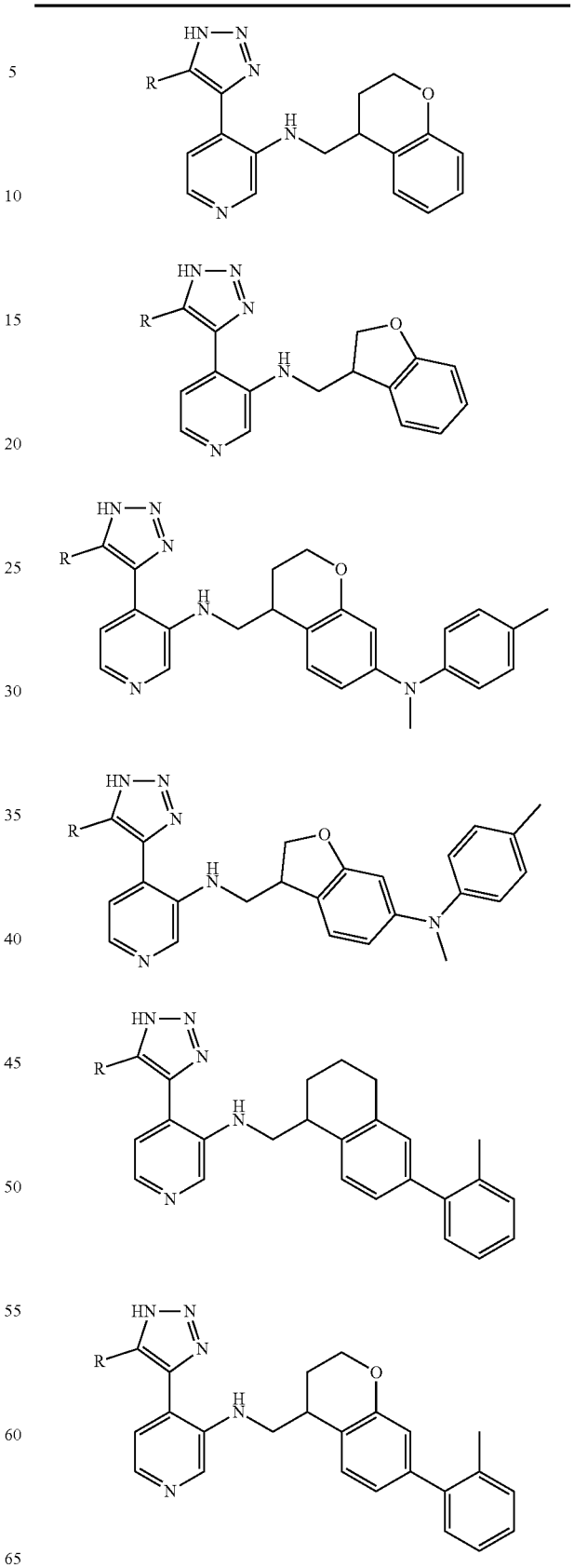

TABLE 2-continued
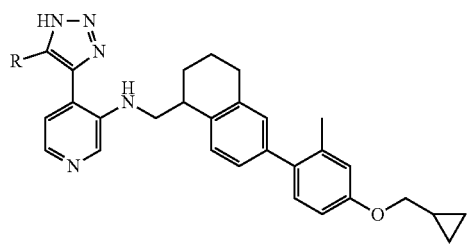
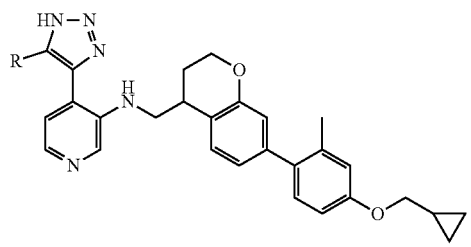
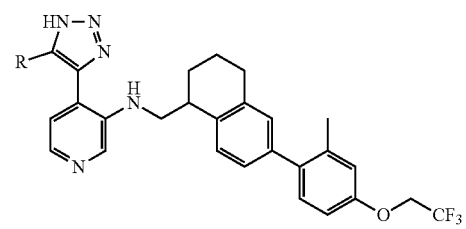
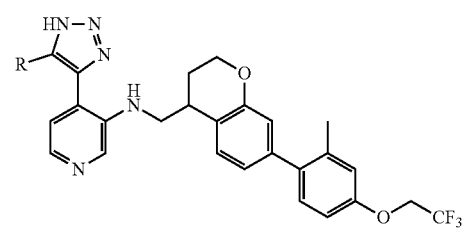
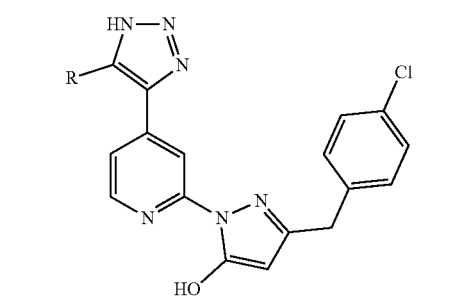
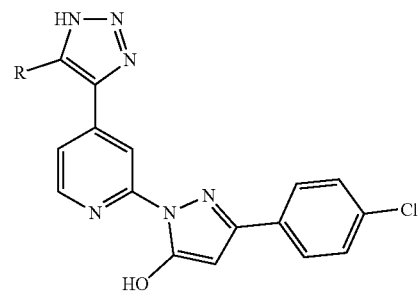
TABLE 2-continued
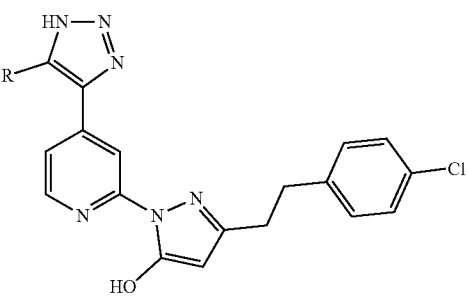
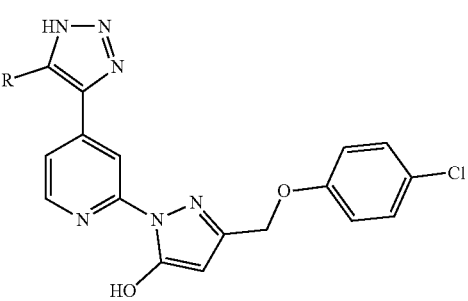
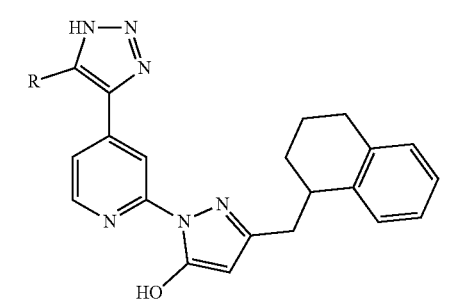
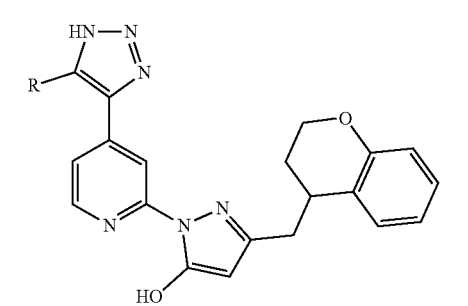
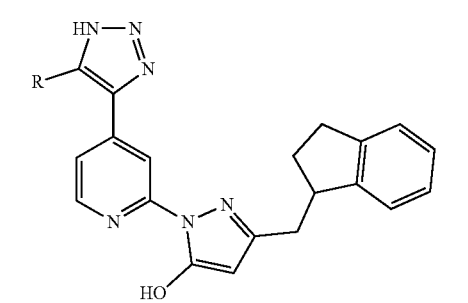

TABLE 2-continued

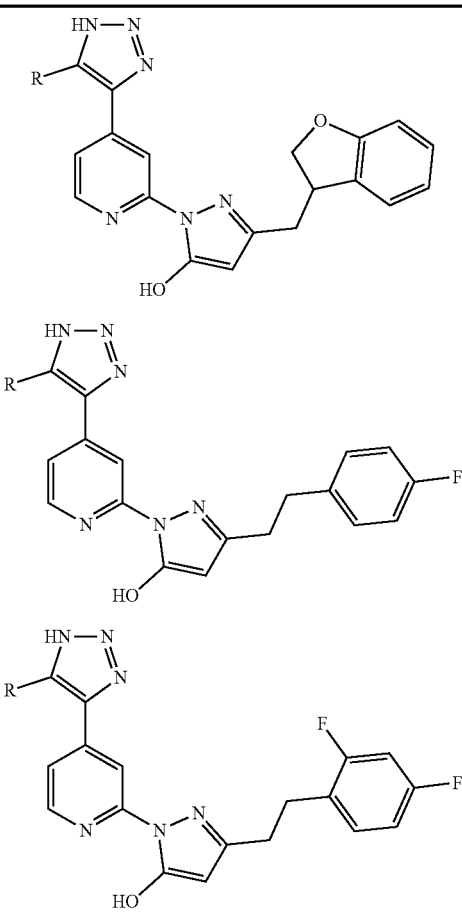

Preparation of the Substituted Triazolylpyridine Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa., US), Aldrich Chemical (Milwaukee, Wis., US; includes Sigma Chemical and Fluka), Apin Chemicals Ltd. (Milton Park, UK), Avocado Research (Lancashire, UK), BDH Inc. (Toronto, CA), Bionet (Cornwall, UK), Chemservice Inc. (West Chester, Pa., US), Crescent Chemical Co. (Hauppauge, N.Y., US), Eastman Organic Chemicals, Eastman Kodak Company (Rochester, N.Y., US), Fisher Scientific Co. (Pittsburgh, Pa., US), Fisons Chemicals (Leicestershire, UK), Frontier Scientific (Logan, Utah, US), ICN Biomedicals, Inc. (Costa Mesa, Calif., US), Key Organics (Cornwall, UK), Lancaster Synthesis (Windham, N.H., US), Maybridge Chemical Co. Ltd. (Cornwall, UK), Parish Chemical Co. (Orem, Utah, US), Pfaltz & Bauer, Inc. (Waterbury, Conn., US), Polyorganix (Houston, Tex., US), Pierce Chemical Co. (Rockford, Ill., US), Riedel de Haen AG (Hanover, DE), Spectrum Quality Product, Inc. (New Brunswick, N.J., US), TCI America (Portland, Or., US), Trans World Chemicals, Inc. (Rockville, Md., US), and Wako Chemicals USA, Inc. (Richmond, Va., US).

Methods known to one of ordinary skill in the art are identified through various reference books and databases. Suitable reference books and treatise that detail the synthesis of reactants useful in the preparation of compounds described herein, or provide references to articles that describe the preparation. See, e.g., SYNTHETIC ORGANIC CHEM. (John Wiley & Sons, Inc., N.Y.); Sandler et al., ORGANIC FUNCTIONAL GROUP PREP., 2nd Ed. (Academic Press, N.Y., 1983); House, MODERN SYNTHETIC REACTIONS, 2nd Ed. (W. A. Benjamin, Inc., Menlo Park, Calif., 1972); Gilchrist, HETEROCYCLIC CHEM., 2nd Ed. (John Wiley & Sons, N.Y., 1992); March, ADVANCED ORGANIC CHEM.: REACTIONS, MECHANISMS & STRUCTURE, 4th Ed., (Wiley-Interscience, N.Y., 1992). Additional suitable references that detail the synthesis of reactants useful in the preparation of compounds described herein, or provide references to articles that describe the preparation, are known in the art. See, e.g., Fuhrhop & Penzlin, ORGANIC SYNTH.: CONCEPTS, METHODS, STARTING MAT'LS, 2nd Revised & Enlarged Ed. (John Wiley & Sons, ISBN: 3-527-29074-5, 1994); HOFFMAN, ORGANIC CHEM., INTERMEDIATE TEXT (Oxford Univ. Press, ISBN 0-19-509618-5, 1996); Larock, COMPREHENSIVE ORGANIC TRANSFORMATIONS: GUIDE TO FUNCTIONAL GROUP PREPARATIONS, 2nd Ed. (Wiley-VCH, ISBN: 0-471-19031-4, 1999); March, ADVANCED ORGANIC CHEM.: REACTIONS, MECHANISMS, & STRUCTURE, 4th Ed. (John Wiley & Sons, ISBN: 0-471-60180-2, 1992); MODERN CARBONYL CHEM. (Otera (Ed.), Wiley-VCH, ISBN: 3-527-29871-1, 2000); Patai, PATAI'S 1992 GUIDE TO CHEM. OF FUNCTIONAL GROUPS (Interscience ISBN: 0-471-93022-9, 1992); Solomons, ORGANIC CHEM., 7th Ed. (John Wiley & Sons, ISBN: 0-471-19095-0, 2000); Stowell, INTERMEDIATE ORGANIC CHEM., 2nd Ed. (Wiley-Interscience, ISBN: 0-471-57456-2, 1993); INDUSTRIAL ORGANIC CHEM.: STARTING MATERIALS & INTERMEDIATES: ULLMANN'S ENCYCLOPEDIA (John Wiley & Sons, ISBN: 3-527-29645-X, 1999) in 8 volumes; ORGANIC REACTIONS (1942-2000) (John Wiley & Sons), in over 55 volumes; CHEM. FUNCTIONAL GROUPS (John Wiley & Sons), in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is Stahl & Wermuth, HANDBOOK OF PHARMACEUTICAL SALTS (Verlag Helvetica Chimica Acta, Zurich, 2002).

General methods for the synthesis of substituted heterocyclic derivatives are also known. See, e.g., WO 2009158396; WO 200563768; WO 2006112666; Briet et. al., 58 Tetrahedron 5761 (2002); WO 200877550; WO 200877551; WO 200877556; WO 200712421; WO 200712422; US200799911; WO 200877550; Havera et al., 42 J. Med. Chem. 3860 (1999); WO 200429051; US20090054434. Additional examples of the synthesis of substituted heterocyclic derivatives are known. See, e.g., WO 2012/171337; WO 2011/044157; WO 2009/097567; WO 2005/030791; EP 203216; Becknell et al., 21 Bioorg. Med. Chem. Letts. 7076 (2011); Svechkarev et al., Visnik Kharkivs'kogo Natsional'nogo Univ. im. V. N. Karazina, 770:201 (2007); Coskun et al., 35 Synth. Commun. 2435 (2005); Alvarez et al., 15 Sci. Synth. 839 (2005); Kihara et al., 53 Heterocycl. 359 (2000); Couture et al., 7 J. Chem. Soc'y, Perkin Transact. 1: Org. Bio-Org. Chem. 789 (1999);

Kihara et al., 48 Heterocycles 2473 (1998); Couture et al., 52 Tetrahed. 4433 (1996); Couturre et al., 37 Tetrahed. Lett. 3697 (1996); Natsugari et al., 38 J. Med. Chem. 3106 (1995); Moehrle et al., 321 Archiv Pharm. 759 (Weinheim, DE) 321:759 (1988); Gore et al., 3 J. Chem. Soc'y, Perkin Transact. 1: Org. Bio-Org. Chem. 481 (1972-1999) (1988); Narasimhan et al., 3 J. Chem. Soc'y, Chem. Commun. 191 (1987); Henry et al., 40 J. Org. Chem. 1760 (1975); Berti, 90 Gazzetta Chim. Italiana 559 (1960); Berti et al., 49 Annal. Chim. 2110 (Rome, Italy) (1959); Berti et al., 49 Annal. Chim. 1253 (Rome, Italy) (1959); WO 2012000595; Couture et al., 52 Tetrahed. 4433 (1996); WO 2010069504; WO 2010069504; WO 2006030032; WO 2005095384; US20050222159; WO 2013064984; Mishra et al., 2013 Eur. J. Org. Chem. 693 (2013); Vachhani et al., 69 Tetrahed. 359 (2013); Xie et al., 45 Eur. J. Med. Chem. 210 (2010); Mukaiyama et al., 15 Bioorg. Med. Chem. 868 (2007); JP2005/089352; Wang et al., 9 Molec. 574 (2004); WO 2000023487; US20060287341; CN103183675; Hares et al., 32 Egyptian J. Pharm. Sci. 303 (1991); DE2356005; DE2133898; DE2133998; U.S. Pat. No. 3,816,422; DE2011970; Staehle et al., 8 Justus Liebigs Annalen der Chem. 1275 (1973).

Additional methods for the synthesis of the substituted heterocyclic derivative compounds disclosed herein are readily available to one of skill in the art. In some embodiments, the substituted heterocyclic derivative compounds disclosed herein are prepared by the general synthetic routes described in the following Schemes 1 and 2, which are exemplary to one of skill in the art and are not limiting.

Scheme 1

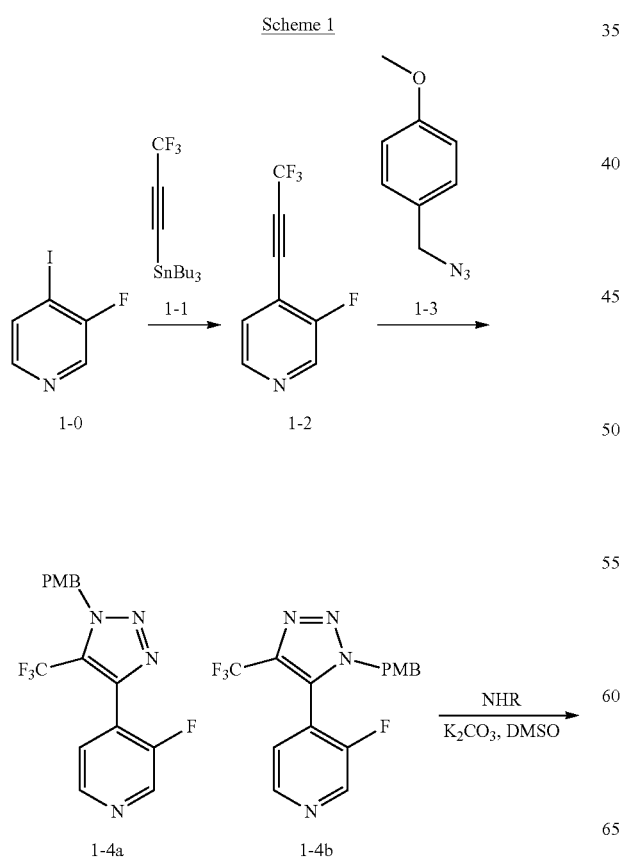

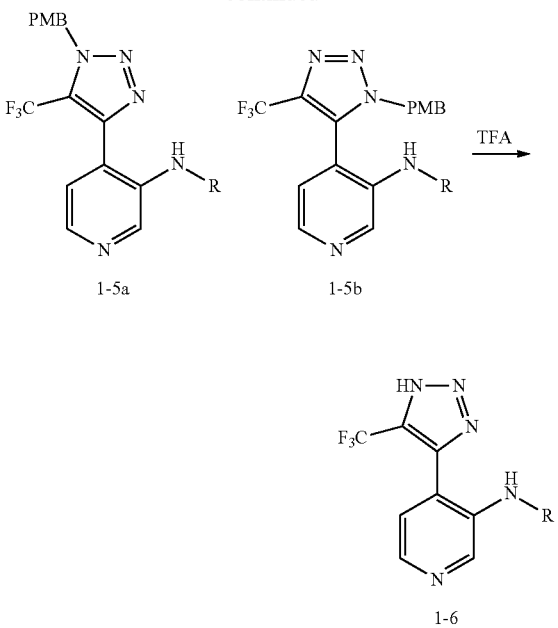

Referring to Scheme 1, above, 3-fluoro-4-iodopyridine (1-0) undergoes a Stille coupling reaction with the tin reagent, tributylstannyl-3,3,3-trifluoro-1-propyne, in presence of a catalytic amount of Pd(0), in toluene, in elevated temperature, such as 130° C., in a microwave oven to give (1-2). It is then heated with 1-azidomethyl-4-methoxy-benzene at reflux in an organic solvent, such as t-butyl alcohol or toluene, to give a mixture of -p-methoxybenzyl-protected (PMB-protected) trifluoromethyl triazole intermediates (1-4a) and (1-4b). Displacement of 3-fluoro group with amines in presence of $K_2CO_3$ in dimethyl sulfoxide (DMSO) at high temperature, such as 180° C., gives mixture (1-5a) and (1-5b), which is then treated with trifluoroacetic acid (TFA) at room temperature (RT) overnight, or at 50° C. for shorter period of time, to give the final product (1-6).

Scheme 2

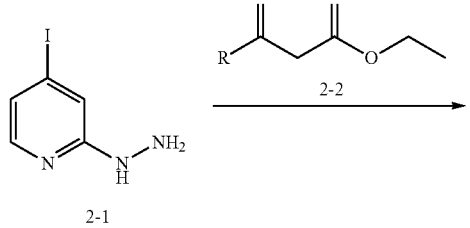

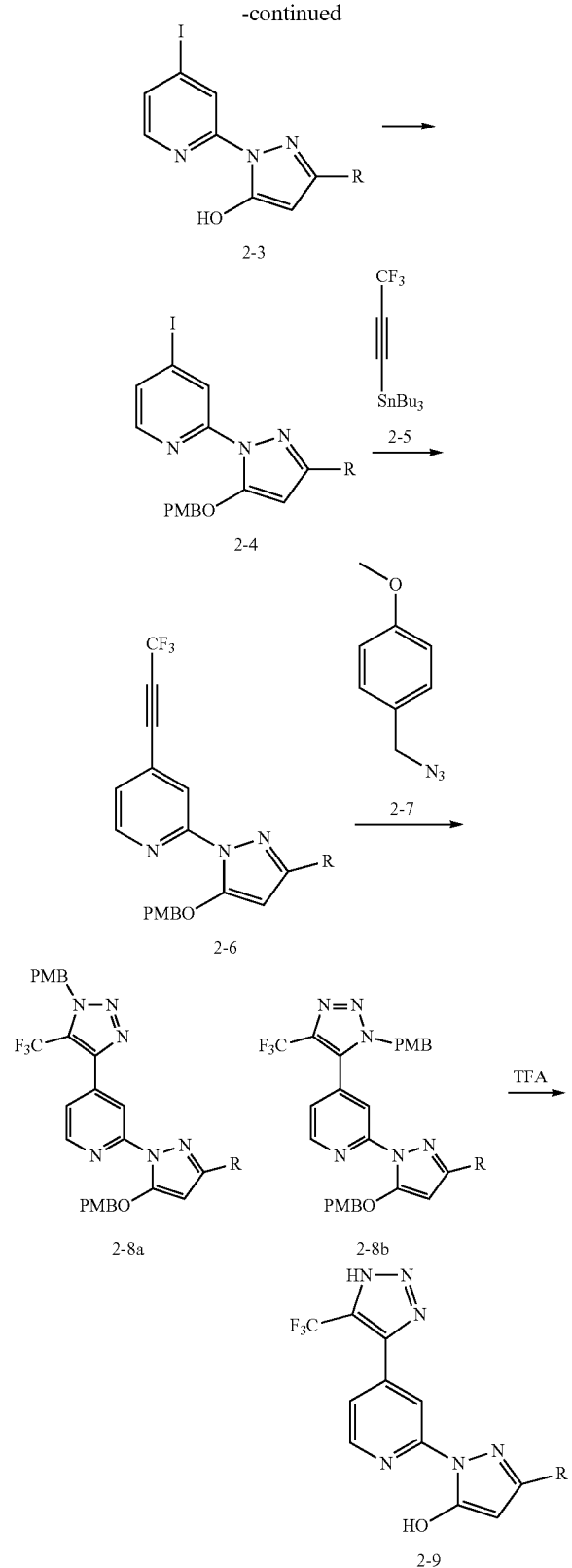

temperature (e.g., about 60° C. to 100° C.) to give intermediate (2-1). Subsequent reaction with an acetoacetyl ester in a mixture of an alcoholic solvent (such as ethanol) heated to reflux in presence of acetic acid provides cyclized hydroxypyrazole pyridine intermediates (2-3). Following a protection of the hydroxyl group by PMB, intermediates (2-4) undergo Stille coupling with the tin reagent, tributylstannyl-3,3,3-trifluoro-1-propyne, in presence of a catalytic amount of Pd(0), in toluene, at elevated temperature, e.g., 120° C., in a microwave oven, to give (2-6). It is then heated with 1-azido-methyl-4-methoxy-benzene at reflux in an organic solvent, such as t-butyl alcohol or toluene, to give a mixture of PMB-protected trifluoromethyl triazole intermediates (2-8a) and (2-8b), which are treated with TFA at room temperature overnight, or at 50° C. for shorter period of time, to give the final product (2-9).

In each of the above reaction procedures or schemes, the various substituents may be selected from among the various substituents otherwise taught herein.

Pharmaceutical Compositions

As noted above, in certain embodiments, the substituted triazolylpyridine derivative compounds as described herein may be administered as a pure chemical or salt thereof. In other embodiments, the substituted triazolylpyridine derivative compounds described herein are prepared in a pharmaceutical composition in which the substituted triazolylpyridine derivative compound is combined with at least one pharmaceutically acceptable or pharmaceutically suitable excipient (also referred to herein as a pharmaceutically suitable (or acceptable) carrier, physiologically suitable (or acceptable) excipient, or physiologically suitable (or acceptable) carrier), selected on the basis of a chosen route of administration and standard pharmaceutical practices, as are well known. See, e.g., REMINGTON: SCI. & PRACTICE PHARM. 21ST ED. (Gennaro, Mack Pub. Co., Easton, Pa., 2005).

Accordingly, provided herein are pharmaceutical compositions that comprise at least one substituted heterocyclic derivative compound, or a stereoisomer, pharmaceutically acceptable salt, hydrate, solvate, or N-oxide thereof, together with at least one pharmaceutically acceptable excipient. The excipient (or carrier) is acceptable or suitable if the excipient is compatible with the other active agents or excipients of the composition, not deleterious to the recipient (i.e., the subject) of the composition, and prepared under good laboratory practices as required for the particular dosage form.

One embodiment provides a pharmaceutical composition comprising a compound of Formula I, or a pharmaceutically acceptable salt thereof. One embodiment provides a pharmaceutical composition comprising a compound of Formula II, or a pharmaceutically acceptable salt thereof.

In certain embodiments, the substituted triazolylpyridine derivative compounds as described herein are substantially pure, in that such compound contains less than about 5%, or less than about 1%, or less than about 0.1%, of other organic small molecules, such as contaminating intermediates or by-products that are created, for example, in one or more of the steps of a synthesis process.

Suitable oral dosage forms include, for example, tablets, pills, sachets, or capsules of hard or soft gelatin, methylcellulose or of another suitable material easily dissolved in the digestive tract. Suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. See, e.g., REMINGTON, 2005.

A method for preparing compounds such as compounds (2-9) is provided in Scheme 2, above. According to this approach, 2-fluoro-4-iodopyridine is treated with hydrazine hydrate in an alcoholic solvent, such as ethanol, at elevated The dose of the composition comprising at least one substituted triazolylpyridine derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient. Oral doses typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known that can covalently modify histones at various sites.

Accordingly, chromatin structure plays a critical role in regulating gene transcription, which cannot occur efficiently in highly condensed chromatin. Chromatin structure is controlled by a series of post translational modifications to histone proteins, notably to histones H3 and H4, and most commonly within the "histone tails" which extend beyond the core nucleosome structure. These post translational modifications include acetylation, methylation, phosphorylation, ribosylation sumoylation, ubiquitination, citrullination, deimination, and biotinylation. In addition to the histone tails, the cores of histones H2A and H3 can be modified. Given the function of histones in chromatin, histone modifications are integral to diverse biological processes such as gene expression, DNA replication, DNA repair, and chromosome condensation.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenosyl methionine (SAM) to histones. Histone methylation is known to participate in a diverse range of biological processes including heterochromatin formation, X-chromosome inactivation, and transcriptional regulation. Lachner et al., 116 J. Cell Sci. 2117-24 (2003); Margueron et al., 15 Curr. Opin. Genet. Devel. 163-76 (2005).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). Methylation of histone residues H3K9, H3K27, and H4K20, is generally linked to gene silencing; and methylation of H3K4, H3K36, and H3K79, is generally associated with active gene expression. In addition, tri- and di-methylation of H3K4 generally marks the transcriptional start sites of actively transcribed genes, whereas mono-methylation of H3K4 is associated with transcriptional enhancer sequences.

A "demethylase" or "protein demethylase," refers herein to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36, or H3K79. Alternately, an H4 demethylase may demethylate histone H4K20. Demethylases are known that can demethylate either a mono-, di- or a tri-methylated substrate. Further, histone demethylases can act on a methylated core histone substrate, a mononucleosome substrate, a dinucleosome substrate, or an oligonucleosome substrate, or a peptide substrate, or chromatin (e.g., in a cell-based assay).

The first lysine demethylase discovered was lysine-specific demethylase 1 (LSD1/KDM1), which uses flavin as a cofactor in demethylating mono- and di-methylated H3K4 or mono- and di-methylated H3K9. A second class of Jumonji C (JmjC) domain-containing histone demethylases were predicted, and then confirmed when a formaldehyde release assay identified a H3K36 demethylase; this histone demethylase was named JmjC domain containing histone demethylase 1 (JHDM1/KDM2A).

Additional JmjC domain-containing proteins were identified subsequently, and they can be phylogenetically clustered into seven subfamilies: JHDM1, JHDM2, JHDM3, JMJD2, JARID, PHF2/PHF8, UTX/UTY, or JmjC domain.

FBXL10 and FBXL11

F-box and leucine-rich repeat protein 10 (FBXL10) and F-box and leucine-rich repeat protein 11 (FBXL11) are multifunctional F-box family proteins that demethylate histone H3 via a hydroxylation-based mechanism. FBXL10, also known as lysine (K)-specific demethylase 2B (KDM2B) or Jumonji C domain-containing histone demethylase 1B (JHDM1B), preferentially demethylates trimethylated H3K4 and dimethylated H3K36, but contains weak or no activity for mono- and tri-methylated H3K36. FBXL10 contains three domains: a catalytic JMJC domain, an F-box domain, and a CXXC DNA-binding domain. The N-terminal JMJC domain coordinates iron and α-ketoglutarate to catalyze demethylation through a hydroxylation-based mechanism. The CXXC DNA-binding domain facilitates FBXL10 preferential binding to transcribed regions of ribosomal RNA, causing repression of ribosomal RNA gene transcription, which ultimately causes inhibition of cell growth and proliferation. FBXL10 is overexpressed in acute myeloid leukemia, bladder carcinoma, and pancreatic ductal adenocarcinoma. Additionally, FBXL10 regulates the expression of Polycomb target genes that encode proteins active as epigenetic regulators essential for stem cell differentiation, thus implicating FBXL10 in tumorigenesis.

FBXL11, also known as KDM2A or JHDM1A, demethylates mono- and di-methylated H3K36. The FBXL11 CXXC DNA-binding domain recognizes non-methylated DNA and targets CpG island regions where it specifically removes H3K36 methylation. Further, FBXL11 is required to maintain a heterochromatic state, and sustain centromeric integrity and genomic stability during mitosis. In addition, FBXL11 is a key negative regulator of NF-KB. Overexpression of FBXL11 has been observed in non-small cell lung cancer cell lines (NSCLC), where FBXL11 upregulates phosphor-ERK1/2 by repressing DUSP3 expression. Negative regulation of gluconeogenic gene expression by FBXL11 results in suppression of two rate-limiting gluconeogenic enzymes that are critical for maintaining blood glucose homeostasis.

Accordingly, at least one additional embodiment provides a method for inhibiting a histone-demethylase enzyme comprising contacting a histone demethylase enzyme with a compound of Formula I or Formula II. An additional embodiment provides a method of inhibiting a histone-demethylase enzyme, wherein the histone-demethylase enzyme comprises a JmjC domain. Yet another additional embodiment provides a method for inhibiting a histone-demethylase enzyme, wherein the histone-demethylase enzyme is FBXL10 or FBXL11.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, particular embodiments provide methods of treating a disease regulated by histone methylation or demethylation in a subject in need thereof by modulating the activity of FBXL10 or FBXL11.

The embodiments further provide a therapeutic method of modulating protein methylation, gene expression, cell proliferation, cell differentiation, or apoptosis in vivo in conditions, illnesses, disorders, infections, or diseases disclosed herein, in particular cancer, inflammatory disease, or viral disease, comprising administering to a subject in need of such therapy a pharmacologically active or therapeutically effective amount of at least one substituted triazolylpyridine derivative compound described herein, which may be administered in a pharmaceutical composition.

The embodiments further provide a method of treating a subject, such as a human, suffering from cancer, a neoplastic disease, or other proliferative disorder. The method comprises administering to a subject in need of such treatment a therapeutically effective amount of at least one substituted triazolylpyridine derivative compound described herein, which functions by inhibiting a demethylase and, in general, by modulating gene expression, to modulate various cellular effects, in particular inducting or repressing gene expression, arresting cell proliferation, inducing cell differentiation, or inducing apoptosis.

The embodiments further relate to a method for treating or ameliorating cancer, neoplastic disease, or another proliferative disorder mediated at least in part by histone demethylase activity, by administering an effective amount of a pharmaceutical composition comprising a substituted triazolylpyridine derivative compound described herein, to a mammal, in particular a human, in need of such treatment. In some aspects, the disease to be treated by the methods of the present embodiments is cancer.

In a further embodiment is the method treating cancer in a subject wherein the cancer pancreatic cancer, prostate cancer, breast cancer, gastric cancer, leukemia, bladder cancer, lung cancer, or melanoma.

Other embodiments and uses will be apparent to one skilled in the art in light of the present disclosures. The following examples are provided merely as illustrative of various embodiments and shall not be construed to limit the invention in any way.

EXAMPLES

Unless otherwise noted, reagents and solvents were used as received from commercial suppliers. Anhydrous solvents and oven-dried glassware were used for synthetic transformations sensitive to moisture or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1A:
3-fluoro-4-(3,3,3-trifluoroprop-1-yn-1-yl)pyridine

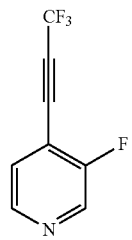

A mixture of 3-fluoro-4-iodopyridine (1 g, 4.48 mmol), 1-tributylstannyl-3,3,3-trifluoro-1-propyne (2.3 g, 5.38 mmol, 90%) and Pd(PPh$_3$)$_4$ (259 mg, 0.045 mmol) in toluene (15 mL) was heated for 5 hr at 130° C. under N$_2$ in a microwave oven. The mixture was concentrated and purified by flash column chromatography on silica gel (EtOAc/Hex=0%-20%) to afford the title compound (260 mg, 31%). [M+H] calculated for C$_8$H$_3$F$_4$N: 190; found: 190.

Preparation 1B: 3-fluoro-4-{1-[(4-methoxyphenyl) methyl]-5-(trifluoromethyl)-1H-1,2,3-triazol-4-yl}pyridine and 3-fluoro-4-{1-[(4-methoxyphenyl) methyl]-4-(trifluoromethyl)-1H-1,2,3-triazol-5-yl}pyridine

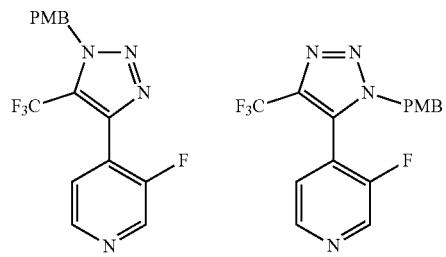

A solution of 3-fluoro-4-(3,3,3-trifluoroprop-1-yn-1-yl) pyridine (260 mg, 1.37 mmol) and 1-azidomethyl-4-methoxy-benzene (4 mL, 2 mmol, 0.5M in methyl t-butyl ether) in t-butanol (10 mL) was heated at 80° C. for 2 hr. The solution was concentrated and purified by flash column chromatography on silica gel (EtOAc/Hex=0%-20%) to afford a mixture of the title compounds (110 mg, 23%). [M+H] calc'd for $C_{16}H_{12}F_4N_4O$: 353; found: 353.

Example 1

3-fluoro-4-[5-(trifluoromethyl)-1H-1,2,3-triazol-4-yl]pyridine

A mixture of 3-fluoro-4-{1-[(4-methoxyphenyl)methyl]-5-(trifluoromethyl)-1H-1,2,3-triazol-4-yl}pyridine and 3-fluoro-4-{1-[(4-methoxyphenyl)methyl]-4-(trifluoromethyl)-1H-1,2,3-triazol-5-yl}pyridine (50 mg, 0.14 mmol) were dissolved in 5 mL of TFA and stirred overnight at 50° C. After the solvent was removed under vacuum, the residue was purified by flash column chromatography to give the title compound (25 mg, 77%). $^1$H NMR (400 MHz, DMSO-d6): δ 7.68 (1H, s), 8.62 (s, 1H), 8.81 (s, 1H). Calc'd for $C_8H_4F_4N_4$: 233; found: 233.

Example 2

N-(5-chloro-2-fluorophenyl)-4-[5-(trifluoromethyl)-1H-1,2,3-triazol-4-yl]pyridin-3-amine

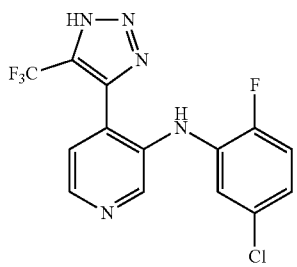 [SMILES: Fc1ccc(Cl)cc1Nc1cnccc1-c1nn[nH]c1C(F)(F)F]

A mixture of 3-fluoro-4-{1-[(4-methoxyphenyl)methyl]-5-(trifluoromethyl)-1H-1,2,3-triazol-4-yl}pyridine and 3-fluoro-4-{1-[(4-methoxyphenyl)methyl]-4-(trifluoromethyl)-1H-1,2,3-triazol-5-yl}pyridine (28 mg, 0.08 mmol), 5-chloro-2-fluoroaniline (17 mg, 0.12 mmol) and $K_2CO_3$ (27 mg, 0.2 mmol) in DMSO (2 mL) was heated at 180° C. for 5 hr in a microwave oven. The reaction mixture was purified by flash column chromatography on silica gel (EtOAc/Hex=0%-20%) to afford an intermediate which was dissolved in 5 mL of TFA and stirred overnight at 50° C. After the solvent was removed under vacuum, the residue was purified by flash column chromatography to give the title compound (5 mg, 17%). $^1$H NMR (400 MHz, DMSO-d6): δ 6.81 (1H, dd, J=2.5 and 7.2 Hz), 6.90 (1H, m), 7.17 (1H, dd, J=2.6 and 8.7 Hz), 7.40 (1H, d, J=5.0 Hz), 8.35 (1H, d, J=5.0 Hz), 8.44 (1H, s). Calculated for $C_{14}H_8ClF_4N_5$: 359; found: 359.

Example 3

N-[(1,2,3,4-tetrahydronaphthalen-1-yl)methyl]-4-[5-(trifluoromethyl)-1H-1,2,3-triazol-4-yl]pyridine-3-amine

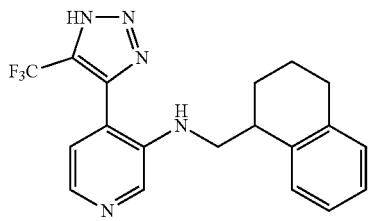 [SMILES: FC(F)(F)c1[nH]nnc1-c1ccncc1NCC1CCCc2ccccc21]

The title compound was prepared in 7% yield according to the general procedure for the synthesis as in Example 2, starting with Preparation 1B. $^1$H NMR (400 MHz, DMSO-d6): δ 1.64-1.75 (4H, m), 2.68 (2H, m), 3.08 (1H, m), 3.51 (2H, m), 7.09 (3H, m), 7.25 (1H, m), 7.39 (1H, m), 8.01 (1H, d, J=4.6 Hz), 8.29 (1H, s). [M+H] calculated for $C_{19}H_{18}F_3N_5$: 374; found: 374.

Preparation 4A: 2-hydrazinyl-4-iodopyridine

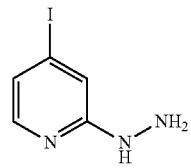

To a solution of 2-fluoro-4-iodopyridine (16 g, 71.74 mmol) in EtOH (160 mL) was added $NH_2NH_2$—$H_2O$ (40 mL). The reaction mixture was stirred overnight at room temp. It was then concentrated in vacuo and the residue was triturated with PE (200 mL) to afford the desired product (16 g, 95%). [M+H] calculated for $C_5H_6IN_3$: 235; found: 235.

Preparation 4B: 3-[(4-chlorophenyl)methyl]-1-(4-iodopyridin-2-yl)-1H-pyrazol-5-ol

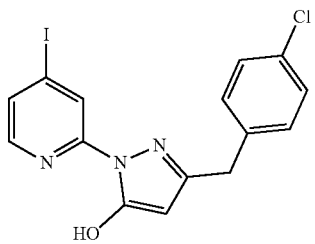 [SMILES: Oc1cc(Cc2ccc(Cl)cc2)nn1-c1cc(I)ccn1]

To a solution of ethyl 4-(4-chlorophenyl)-3-oxobutanoate (2 g, 8.30 mmol) in EtOH (20 mL) was added a solution of 2-hydrazinyl-4-iodopyridine (1.94 g, 8.30 mmol) in EtOH (20 mL) at 50° C., then stirred for 1 hr at 50° C. Then, 5 mL $CH_3COOH$ was added and the mixture was refluxed overnight, then concentrated and the residue dissolved in DCM and washed by aq $Na_2CO_3$, dried, concentrated, and purified by flash column chromatography on silica gel (PE/EA=5/1 to 1/1), to give the title compound (1.9 g, 56%). [M+H] calculated for $C_{15}H_{11}ClIN_3O$: 412; found: 412.

Preparation 4C: 2-{3-[(4-chlorophenyl)methyl]-5-[(4-methoxyphenyl)methoxy]-1H-pyrazol-1-yl}-4-iodopyridine

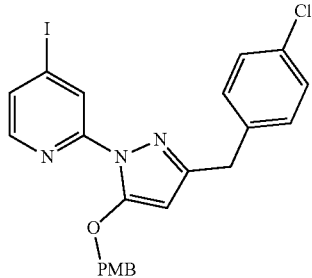

To a mixture of 3-[(4-chlorophenyl)methyl]-1-(4-iodopyridin-2-yl)-1H-pyrazol-5-ol (1 g, 2.43 mmol) and $K_2CO_3$ (470 mg, 3.41 mmol) in DMF (20 mL) was added PMBCl (457 mg, 2.92 mmol) at 0° C., then stirred for 1 hr at 60° C. After concentration, the residue was purified by flash column chromatography on silica gel (PE/EA=10/1 to 3/1) to give the title compound (430 mg, 33%). [M+H] calc'd for $C_{23}H_{19}ClIN_3O_2$: 532; found: 532.

Preparation 4D: 2-{3-[(4-chlorophenyl)methyl]-5-[(4-methoxyphenyl)methoxy]-1H-pyrazol-1-yl}-4-(3,3,3-trifluoroprop-1-yn-1-yl)pyridine

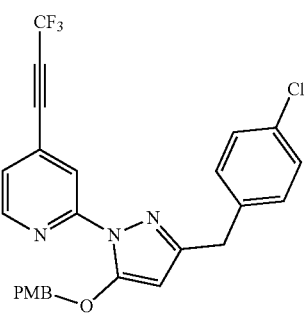

A mixture of 2-{3-[(4-chlorophenyl)methyl]-5-[(4-methoxyphenyl)methoxy]-1H-pyrazol-1-yl}-4-iodopyridine (430 mg, 0.81 mmol), 1-tributylstannyl-3,3,3-trifluoro-1-propyne (363 mg, 0.85 mmol, 90%) and Pd(Ph$_3$)$_4$ (88 mg, 0.081 mmol) in toluene (15 mL) was stirred for 2 hr at 120° C. under N$_2$ in a microwave oven. The mixture was concentrated and purified by flash column chromatography on silica gel (PE/EA=10/1 to 3/1) to afford the title compound (211 mg, 52%). [M+H] calculated for $C_{26}H_{19}ClF_3N_3O_2$: 498; found: 498.

Preparation 4E: 2-{3-[(4-chlorophenyl)methyl]-5-[(4-methoxyphenyl)methoxy]-1H-pyrazol-1-yl}-4-{1-[(4-methoxyphenyl)methyl]-5-(trifluoromethyl)-1H-1,2,3-triazol-4-yl}pyridine and 2-{3-[(4-chlorophenyl)methyl]-5-[(4-methoxyphenyl)methoxy]-1H-pyrazol-1-yl}-4-{1-[(4-methoxyphenyl)methyl]-4-(trifluoromethyl)-1H-1,2,3-triazol-5-yl}pyridine

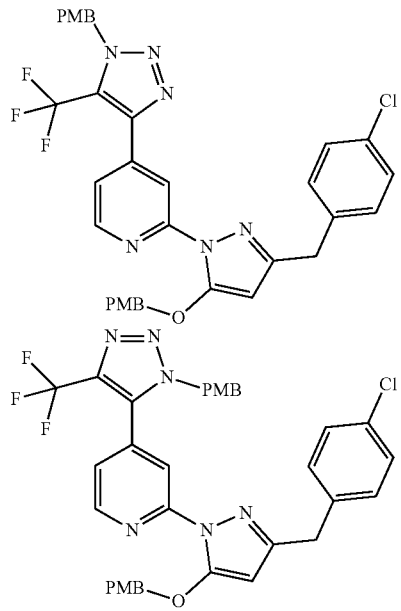

A solution of 2-{3-[(4-chlorophenyl)methyl]-5-[(4-methoxyphenyl)methoxy]-1H-pyrazol-1-yl}-4-(3,3,3-trifluoroprop-1-yn-1-yl)pyridine (210 mg, 0.42 mmol) and 1-azido-methyl-4-methoxy-benzene (71 mg, 0.42 mmol) in toluene (20 mL) was refluxed for 22 hr. The solution was concentrated and purified by flash column chromatography on silica gel (PE/EA=10/1 to 3/1) to afford a mixture of the title compounds (226 mg, 81%). [M+H] calculated for $C_{34}H_{28}ClF_3N_6O_3$: 661; found, 661.

Example 4

3-[(4-chlorophenyl)methyl]-1-{4-[5-(trifluoromethyl)-1H-1,2,3-triazol-4-yl]pyridine-2-yl}-1H-pyrazol-5-ol

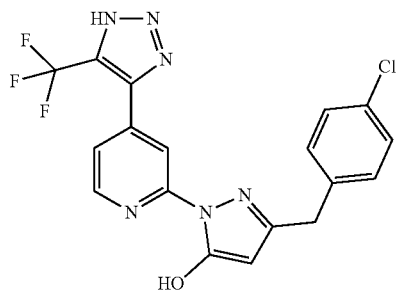 [SMILES: Oc1cc(Cc2ccc(Cl)cc2)nn1-c1cc(-c2nn[nH]c2C(F)(F)F)ccn1]

A solution of 2-{3-[(4-chlorophenyl)methyl]-5-[(4-methoxyphenyl)methoxy]-1H-pyrazol-1-yl}-4-{1-[(4- methoxyphenyl)methyl]-5-(trifluoromethyl)-1H-1,2,3-triazol-4-yl} pyridine (120 mg, 0.18 mmol) in TFA (5 mL) was stirred for 1 hr at 50° C., after concentration the residue was purified by prep-HPLC to give the title compound (30 mg, 39%). $^1$H NMR (400 MHz, DMSO): δ 3.88 (2H, s), 5.24 (1H, br), 7.34-7.51 (6H, m), 8.60 (1H, d, J=5.6 Hz). [M+H] calculated for $C_{18}H_{12}ClF_3N_6O$: 421; found: 421.

Example 5

In Vitro Enzyme Inhibition Assay

This assay determines the ability of a test compound to inhibit FBXL11, FBXL10, and PHF8 demethylase activity. Baculovirus-expressed FBXL11 (GenBank Accession #NM-012308, AA1-1162) was purchased from BPS Bioscience (Cat #50102). Baculovirus-expressed FBXL10 (GenBank Accession #NM-032590, AA 1-650) was purchased from BPS Bioscience (Cat #50120). Baculovirus-expressed PHF8 (GenBank Accession NP-055922.1) was purchased from Active Motif (Cat #31435).

FBXL11 Assay

The ability of test compounds to inhibit the activity of FBXL11 was determined in 384-well plate format under the following reaction conditions: 0.15 nM FBXL11, 30 nM H3K36me2-biotin labeled peptide (Anaspec cat #64442), 0.2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, 5 µM ammonium ironII sulfate. Reaction product was determined quantitatively by AlphaScreen detection after the addition of detection reagents anti-H3K36me1 antibody, AlphaScreen® Streptavidin-coated Donor beads, and AlphaScreen® Protein A Acceptor beads in 50 mM HEPES, pH7.3, 10 mM NaCl, 0.005% Brij35, 5 mM EDTA, 2 mg/ml BSA to a final 10 µg/ml beads.

The assay reaction was initiated by the following: 3 µl of the mixture of 90 nM H3K36me2-biotin labeled peptide and 0.6 µM alpha-ketoglutaric acid with 3 µl of 11-point serial diluted inhibitor in 3% DMSO were added to each well of 384-well Proxiplate (Perkin Elmer), followed by the addition of 3 µl of 0.45 nM FBXL11 to initiate the reaction. The reaction mixture was incubated at room temp for 1 hr, and terminated by the addition of 3 µl of appropriate dilution of anti-H3K36me1 antibody in 50 mM HEPES, pH7.3, 10 mM NaCl, 0.005% Brij35, 5 mM EDTA, and 2 mg/ml BSA. Plates were then incubated at room temp for 40 min, followed by addition of 3 µl of 50 µg/ml AlphaScreen® Streptavidin-coated Donor beads and AlphaScreen® Protein A Acceptor beads in 50 mM HEPES, pH7.3, 10 mM NaCl, 0.005% Brij35, 5 mM EDTA, 2 mg/ml BSA. Plates were read by EnVision Multilabel Reader in AlphaScreen mode after minimum 2 hr incubation at room temp. The AlphaScreen signal for each well is used to determine inhibition constant ($IC_{50}$).

FBXL10 Assay

The ability of test compounds to inhibit the activity of FBXL10 was determined in 384-well plate format under the following reaction conditions: 0.3 nM FBXL10, 30 nM H3K36me2-biotin labeled peptide (Anaspec cat #64442), 0.2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, 5 µM ammonium ironII sulfate. Reaction product was determined quantitatively by AlphaScreen detection after the addition of detection reagents anti-H3K36me1 antibody, AlphaScreen® Streptavidin-coated Donor beads, and AlphaScreen® Protein A Acceptor beads in 50 mM HEPES, pH7.3, 10 mM NaCl, 0.005% Brij35, 5 mM EDTA, 2 mg/ml BSA to a final 10 µg/ml beads.

The assay reaction was initiated by the following: 3 µl of the mixture of 90 nM H3K36me2-biotin labeled peptide and 0.6 µM alpha-ketoglutaric acid with 3 µl of 11-point serial diluted inhibitor in 3% DMSO were added to each well of 384-well Proxiplate (Perkin Elmer), followed by the addition of 3 µl of 0.9 nM FBXL10 to initiate the reaction. The reaction mixture was incubated at room temp for 1 hr, and terminated by the addition of 3 µl of appropriate dilution of anti-H3K36me1 antibody in 50 mM HEPES, pH7.3, 10 mM NaCl, 0.005% Brij35, 5 mM EDTA, and 2 mg/ml BSA. Plates were then incubated at room temp for 40 min, followed by addition of 3 µl of 50 µg/ml AlphaScreen® Streptavidin-coated Donor beads and AlphaScreen® Protein A Acceptor beads in 50 mM HEPES, pH7.3, 10 mM NaCl, 0.005% Brij35, 5 mM EDTA, 2 mg/ml BSA. Plates were read by EnVision Multilabel Reader in AlphaScreen mode after minimum 2 hr incubation at room temp. The AlphaScreen signal for each well is used to determine inhibition constant ($IC_{50}$).

PHF8 Assay

The ability of test compounds to inhibit the activity of PHF8 was determined in 384-well plate format under the following reaction conditions: 3 nM PHF8, 200 nM H3K9me1-biotin labeled peptide (Anaspec cat #64358), 0.5 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 5 µM ammonium ironII sulfate. Reaction product was determined quantitatively by TR-FRET after the addition of detection reagent Phycolink Streptavidin-allophycocyanin (Prozyme) and Europium-anti-unmodified-histone H3 lysine 9/lysine27 (H3K9/K27) antibody (PerkinElmer) in the presence of 5 mM EDTA in LANCE detection buffer (PerkinElmer) at a final concentration of 25 nM and 0.5 nM, respectively.

The assay reaction was initiated by the following: 2 µl of the mixture of 600 nM H3K9me1-biotin labeled peptide and 1.5 µM alpha-ketoglutaric acid with 2 µl of 11-point serial diluted inhibitor in 3% DMSO were added to each well of the plate, followed by the addition of 2 µl of 9 nM PHF8 to initiate the reaction. The reaction mixture was incubated at room temp for 15 min, and terminated by the addition of 6 µl of 5 mM EDTA in LANCE detection buffer containing 50 nM Phycolink Streptavidin-allophycocyanin and 1 nM Europium-anti-unmodified H3K9/K27 antibody. Plates were read by EnVision Multilabel Reader in TR-FRET mode (excitation at 320 nm, emission at 615 nm and 665 nm) after 1 hr incubation at RT. A ratio was calculated (665/615) for each well and fitted to determine inhibition constant ($IC_{50}$).

Example 6

In Vitro Enzyme Inhibition Assay

This assay determines the ability of a test compound to inhibit Jarid1B, JMJD2C and JMJD3 demethylase activity. Baculovirus-expressed Jarid1B (GenBank Accession #NM-006618, AA 2-751) was purchased from BPS Bioscience (Cat #50121) or custom made by MolecularThroughput. Baculovirus-expressed JMJD2C (GenBank Accession #BC143571, AA 2-372) was purchased from BPS Bioscience (Cat #50105). Baculovirus-expressed JMJD3 (GenBank Accession #NM-001080424, AA1043-end) was purchased from BPS Bioscience (Cat #50115).

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium ironII sulfate. Reaction product was determined quantitatively by TR-FRET after the addition of detection reagent Phycolink Streptavidin-allophycocyanin (Prozyme) and Europium-anti-mono- or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 μl of the mixture of 900 nM H3K4me3-biotin labeled peptide and 6 μM alpha-ketoglutaric acid with 2 μl of 11-point serial diluted inhibitor in 3% DMSO was added to each well of the plate, followed by the addition of 2 μl of 2.4 nM Jarid1B to initiate the reaction. The reaction mixture was incubated at room temp for 30 min, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hr incubation at room temp. A ratio was calculated (665/615) for each well and fitted to determine inhibition constant ($IC_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium ironII sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM alpha-ketoglutaric acid with 2 μl of 11-point serial diluted inhibitor in 3% DMSO were added to each well of the plate, followed by the addition of 2 μl of 0.9 nM JMJD2C to initiate the reaction. The reaction mixture was incubated at room temp for 30 min, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hr incubation at RT. A ratio was calculated (665/615) for each well and fitted to determine inhibition constant ($IC_{50}$).

MJD3 Assay

The ability of test compounds to inhibit the activity of JMJD3 was determined in 384-well plate format under the following reaction conditions: 1 nM JMJD3, 250 nM H3K27me3-biotin labeled peptide (Anaspec cat #64367), 1 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, 5 μM ammonium ironII sulfate. Reaction product is determined quantitatively by AlphaScreen detection after the addition of detection reagents anti-H3K27me1 antibody, 5 μg/ml AlphaScreen® Streptavidin-coated Donor beads, and 5 μg/ml AlphaScreen® Protein A Acceptor beads in 50 mM HEPES, pH7.3, 10 mM NaCl, 0.005% Brij35, 10 mM EDTA, 2 mg/ml BSA.

The assay reaction was initiated by the following: 3 μl of the mixture of 750 nM H3K27me3-biotin labeled peptide and 3 μM alpha-ketoglutaric acid with 3 μl of 11-point serial diluted inhibitor in 3% DMSO are added to each well of 384-well Proxiplate (Perkin Elmer), followed by the addition of 3 μl of 3 nM JMJD3 to initiate the reaction. The reaction mixture was incubated at room temp for 20 min, and terminated by the addition of 3 μl of appropriate dilution of anti-H3K27me1 antibody in 50 mM HEPES, pH7.3, 10 mM NaCl, 0.005% Brij35, 10 mM EDTA, 2 mg/ml BSA. Plates were incubated at RT for 1 hr, followed by addition of 3 μl of 25 μg/ml AlphaScreen® Streptavidin-coated Donor beads and AlphaScreen® Protein A Acceptor beads in 50 mM HEPES, pH7.3, 10 mM NaCl, 0.005% Brij35, 10 mM EDTA, 2 mg/ml BSA. Plates were read by EnVision Multilabel Reader in AlphaScreen mode after minimum 2 hr incubation at room temp. The AlphaScreen signal for each well was used to determine inhibition constant ($IC_{50}$).

The ability to inhibit demethylase activity was quantified and the respective $IC_{50}$ value was determined for substituted triazolylpyridine derivative compounds. Table 3 provides the $IC_{50}$ values, in μM, of various compounds disclosed herein; in which the biochemical assay $IC_{50}$ data are designated in the following ranges A: ≤0.10 μM; B: >0.10 μM to ≤1.0 μM; C: >1.0 μM to ≤10 μM; and D: >10 μM.

TABLE 3

| Chemical Synthesis Example | Name | FBXL10 | JARID1B | JMJD2C | JMJD3 |
|---|---|---|---|---|---|
| 1 | 3-fluoro-4-[5-(trifluoromethyl)-1H-1,2,3-triazol-4-yl]pyridine | B | D | D | D |
| 2 | N-(5-chloro-2-fluorophenyl)-4-[5-(trifluoromethyl)-1H-1,2,3-triazol-4-yl]pyridin-3-amine | C | D | D | D |
| 3 | N-[(1,2,3,4-tetrahydronaphthalen-1-yl)methyl]-4-[5-(trifluoromethyl)-1H-1,2,3-triazol-4-yl]pyridin-3-amine | C | D | D | D |

Example 7

Preparation of Pharmaceutical Dosage Forms: Oral Tablet

A tablet is prepared by mixing 48% by weight of a compound of Formula I or Formula II, or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250 mg-500 mg.

We claim:

1. A method of inhibiting a histone demethylase enzyme selected from a group comprising FBXL10, JARID1B, JMJD2C and JMJD3 comprising contacting a histone demethylase enzyme with an effective amount of a compound of Formula II

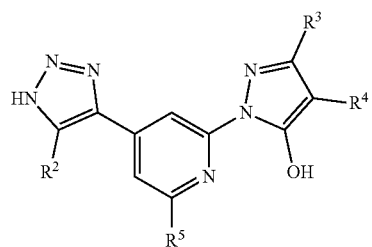

Formula II wherein a compound of Formula II is optionally a pharmaceutically acceptable salt thereof, and wherein
$R^2$ is halogen or —$CF_3$;
$R^3$ is hydrogen, halogen, —OH, —$OR^6$, —$N(R^6)_2$, or alkyl, carbocyclyl, aryl optionally substituted with halogen, carbocyclylalkyl, or aralkyl optionally substituted with halogen or alkyl;
$R^4$ is hydrogen, halogen, —OH, —$OR^6$, —$N(R^6)_2$, or alkyl, carbocyclyl, aryl, carbocyclylalkyl, or aralkyl; wherein
each $R^6$ is independently hydrogen, or optionally substituted alkyl, carbocyclyl, aryl, carbocyclylalkyl, or aralkyl; and
$R^5$ is hydrogen, methyl, ethyl, isopropyl, t-butyl, —$CHF_2$, —$CH_2F$, —$CF_3$, —$CH_2OH$, —$CHCH_3OH$, or —$C(CH_3)_2OH$.

2. The method of claim 1, wherein $R^2$ is chloro or fluoro.

3. The method of claim 1, wherein $R^4$ and $R^5$ are hydrogen, and $R^3$ is aralkyl optionally substituted with halogen or alkyl, or cycloalkyl.

4. The method of claim 1, having the structure:

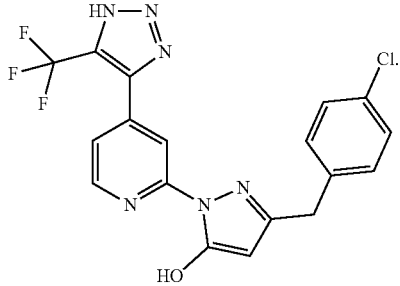 [SMILES: Oc1cc(Cc2ccc(Cl)cc2)nn1-c1cc(-c2nn[nH]c2C(F)(F)F)ccn1]

\* \* \* \* \*